(12) United States Patent
Fang et al.

(10) Patent No.: US 9,115,347 B2
(45) Date of Patent: Aug. 25, 2015

(54) METHODS AND COMPOSITIONS FOR INCREASING TOXIN PRODUCTION

(75) Inventors: Aiqi Fang, Long Grove, IL (US);
Andrew James White, Ascot Vale (AU);
Seshu Tummala, Groveland, MA (US);
Lee Wilson, Weymouth, MA (US)

(73) Assignee: Sanofi Pasteur Biologies, LLC, Cambridge, MA (US)

( * ) Notice: Subject to any disclaimer, the term of this patent is extended or adjusted under 35 U.S.C. 154(b) by 206 days.

(21) Appl. No.: 13/120,510

(22) PCT Filed: Sep. 24, 2009

(86) PCT No.: PCT/US2009/058268
§ 371 (c)(1),
(2), (4) Date: Jul. 7, 2011

(87) PCT Pub. No.: WO2010/036826
PCT Pub. Date: Apr. 1, 2010

(65) Prior Publication Data
US 2011/0256606 A1    Oct. 20, 2011

Related U.S. Application Data

(60) Provisional application No. 61/099,759, filed on Sep. 24, 2008.

(51) Int. Cl.
| | |
|---|---|
| *C12P 21/04* | (2006.01) |
| *C12N 15/09* | (2006.01) |
| *A61K 39/02* | (2006.01) |
| *A61K 39/08* | (2006.01) |
| *C12N 1/20* | (2006.01) |
| *C12P 21/02* | (2006.01) |

(52) U.S. Cl.
CPC .. *C12N 1/20* (2013.01); *C12P 21/02* (2013.01)

(58) Field of Classification Search
CPC ........... C12P 7/065; C12P 21/04; C12N 1/04; C12N 1/20; C12N 1/38; C12N 10/02; C12N 15/09
See application file for complete search history.

(56) References Cited

U.S. PATENT DOCUMENTS

2004/0235139 A1* 11/2004 Demain et al. ............. 435/252.7
2007/0207531 A1*  9/2007 Ferchichi et al. ............. 435/168
2007/0231336 A1   10/2007 Thomas et al.

OTHER PUBLICATIONS

Maegawa et al., (J. Med. Microbiol. 2002. vol. 51: 34-41).*
Onderdonk et al., (Applied and Environ. Microbio. 1979. vol. 38(4): 637-641).*
Demain (SIM Annual Meeting and Exhibition. Jul. 29-Aug. 2, 2007. Thursday, Aug. 2, 2007—9:00am).*
Yamakawa et al., (J. Med Microbiol. 1996. vol. 44:111-114).*
Nakamura et al., (Microbio. Immunol. 1981. vol. 25(9):863-70).*
Benno et al., "Comparison of Fecal Microflora of Elderly Persons in Rural and Urban Areas of Japan," Applied Environ. Microbiol. 55:1100-1105, 1989.
Hafiz et al., "*Clostridium difficile*: Isolation and Characteristics," J. Med. Microbiol. 9:129-137, 1976.

(Continued)

*Primary Examiner* — Ja'Na Hines
(74) *Attorney, Agent, or Firm* — Clark & Elbing LLP; Susan M. Michaud

(57) ABSTRACT

The invention provides methods and compositions (such as for example, culture media) for culturing *Clostridium difficile* and producing the *C. difficile* Toxins A and B.

10 Claims, 19 Drawing Sheets

(56) References Cited

OTHER PUBLICATIONS

Hussain et al., "Development and Evaluation of a Cocultural Technique for Identification of Anaerobic Organisms," J. Clin. Microbiol. 19:215-217, 1984.

Karlsson et al., "Toxin, Butyric Acid, and Other Short-Chain Fatty Acids are Coordinately Expressed and Down-Regulated by Cysteine in Clostridium difficile," Infection and Immunity 68:5881-5888, 2000.

Maegawa et al., "Linkage Between Toxin Production and Purine Biosynthesis in Clostridium difficile," J. Med. Microbiol. 51:34-41, 2002.

Marler et al., "Comparison of Five Cultural Procedures for Isolation of Clostridium difficile from Stools," J. Clin. Microbiol. 30:514-516, 1992.

Moore et al., "Identification of Intrinsic High-Level Resistance to Rare-Earth Oxides and Oxyanions in Members of the Class Proteobacteria: Characterization of Tellurite, Selenite, and Rhodium Sesquioxide Reduction in Rhodobacter sphaeroides," J. Bacteriology 174:1505-1514, 1992.

Onderdonk et al., "Effect of Environmental Stress on Clostridium difficile Toxin Levels During Continuous Cultivation," Applied Environ. Microbiol. 38:637-641, 1979.

International Search Report from International Application No. PCT/US2009/058268, dated Nov. 8, 2009 (date of completion of report) and Dec. 9, 2009 (date of mailing of report).

Written Opinion from International Application No. PCT/US2009/058268, dated Nov. 8, 2009 (date of completion of opinion) and Dec. 9, 2009 (date of mailing of opinion).

International Preliminary Report on Patentability from International Application No. PCT/US2009/058268, dated Mar. 29, 2011.

Drummond et al., "Effects of Sub-MIC Concentrations of Antibiotics on Growth of and Toxin Production by Clostridium difficile," J. Med. Microbiol. 52:1033-1038, 2003.

Karlsson et al., "Induction of Toxins in Clostridium difficile is Associated with Dramatic Changes of its Metabolism," Microbiol. 154:3430-3436, 2008.

Luli et al., "Hexavalent Chromium-Resistant Bacteria Isolated from River Sediments," App. Environ. Microbiol. 46:846-854, 1983.

Extended European Search Report from European Patent Application No. 09816870.1 dated Jul. 3, 2012 (date of mailing of report) and Jun. 19, 2012 (date of completion of search).

* cited by examiner

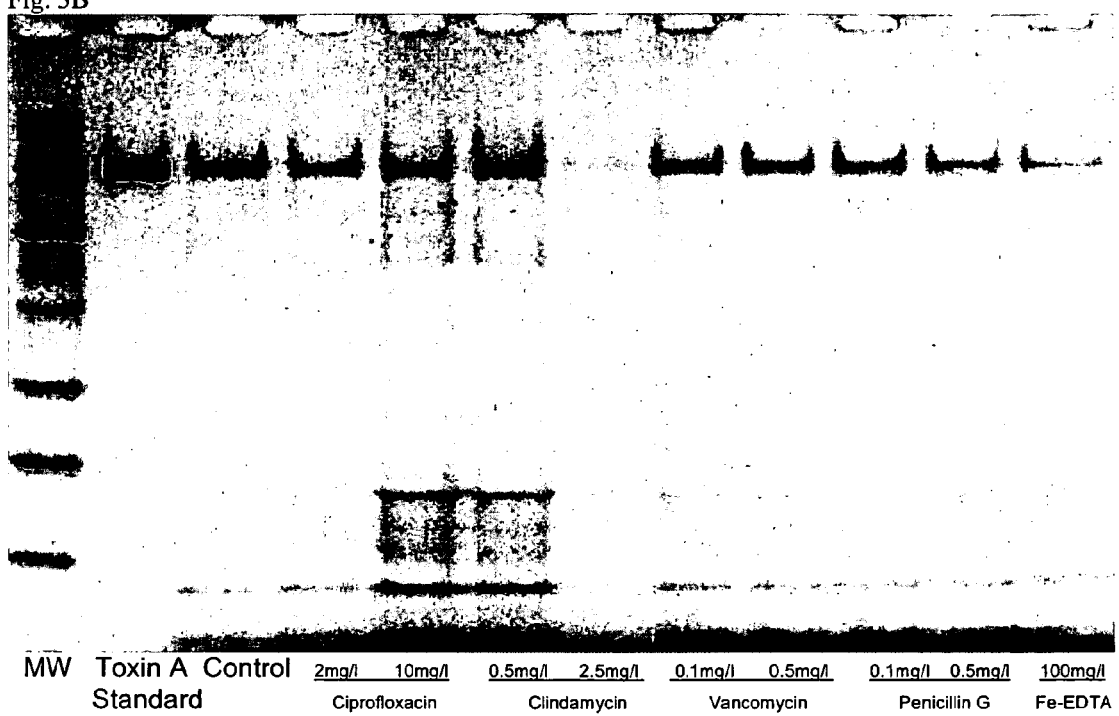

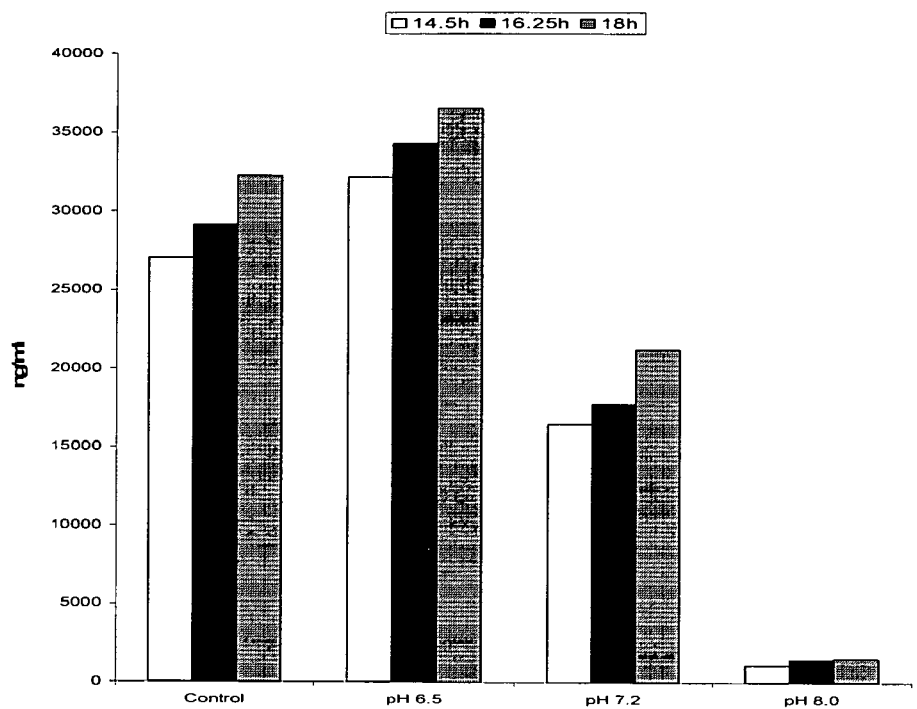
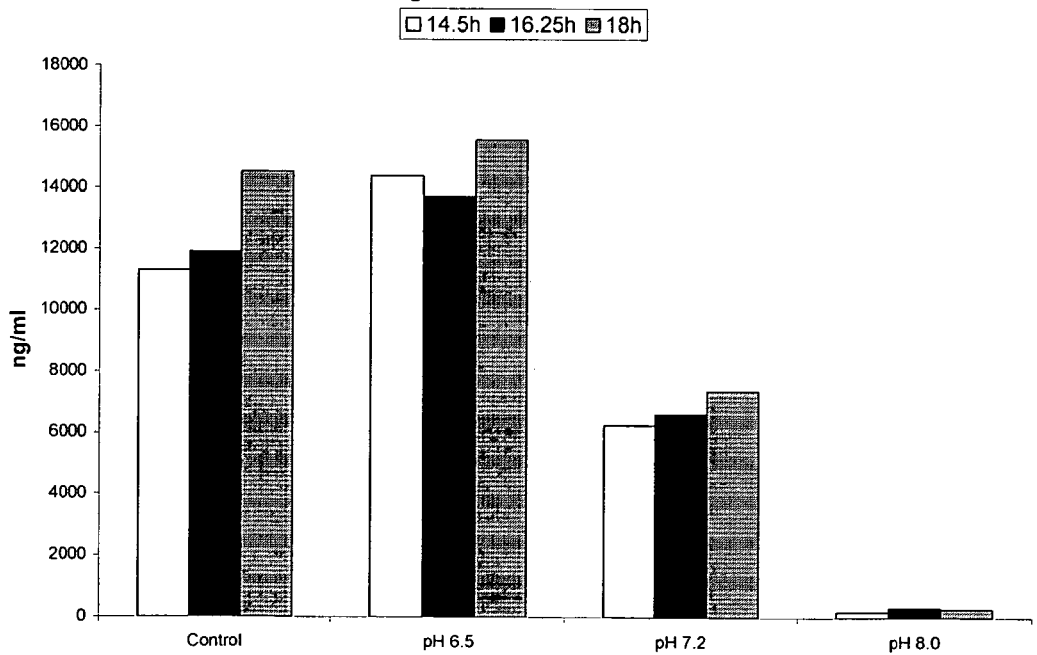

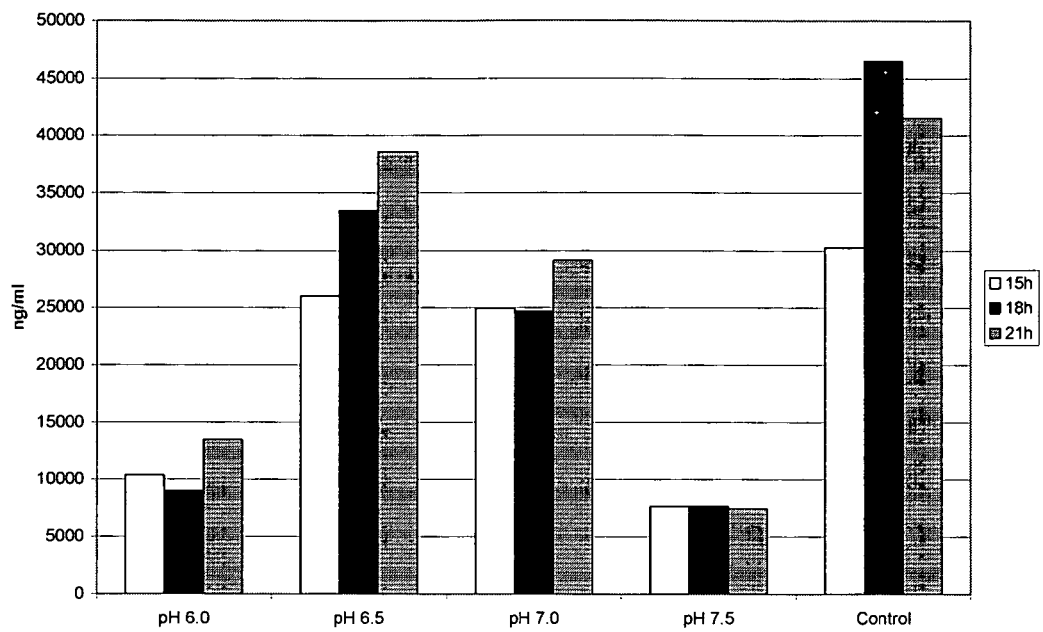
Fig. 7A Toxin A Yield
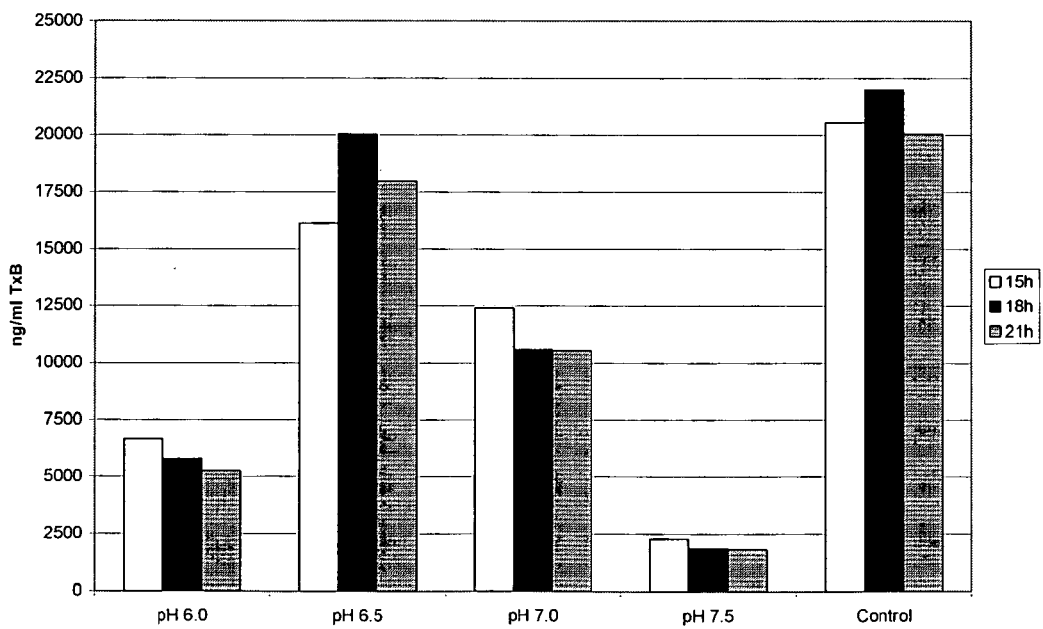
Fig. 7B Toxin B Yield

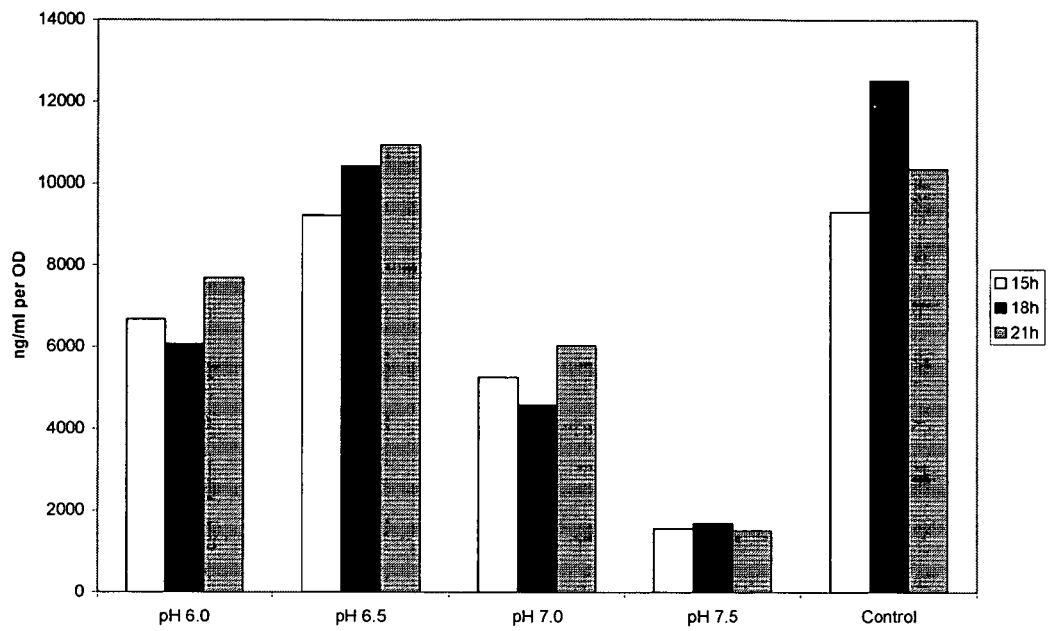
Fig. 7C: Specific Toxin A Productivity
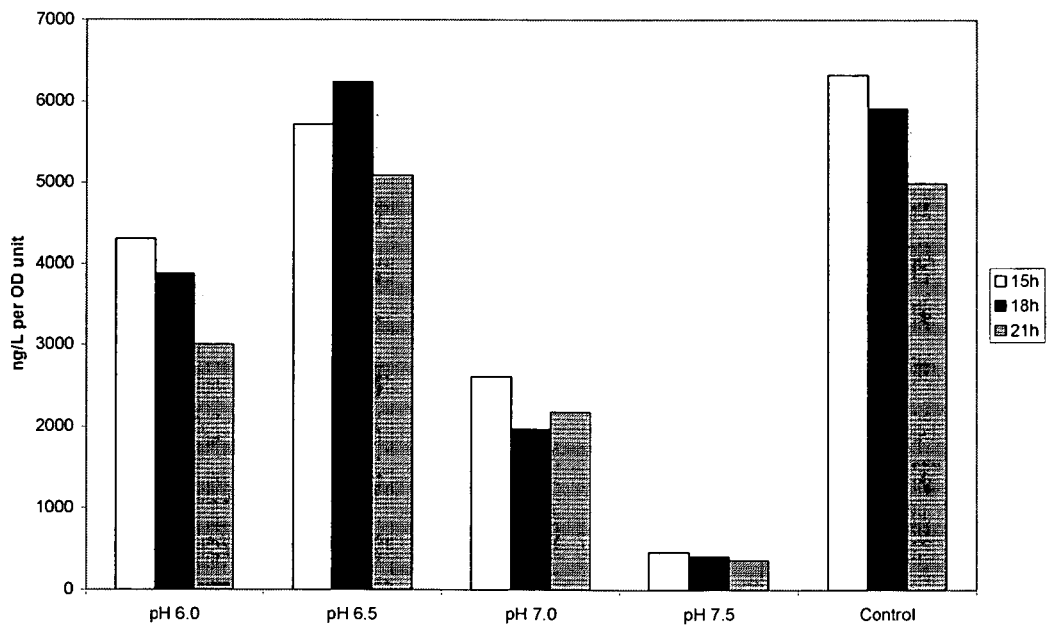
Fig. 7D: Specific Toxin B Productivity

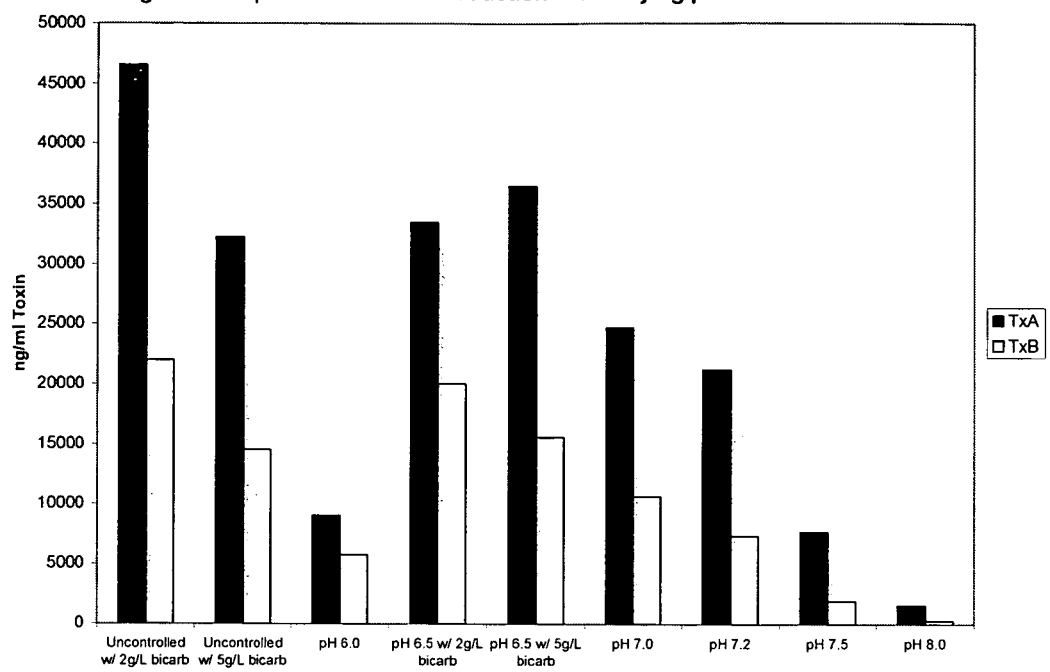

Fig. 8A: Toxin A Yield

Fig. 8B: Toxin B Yield

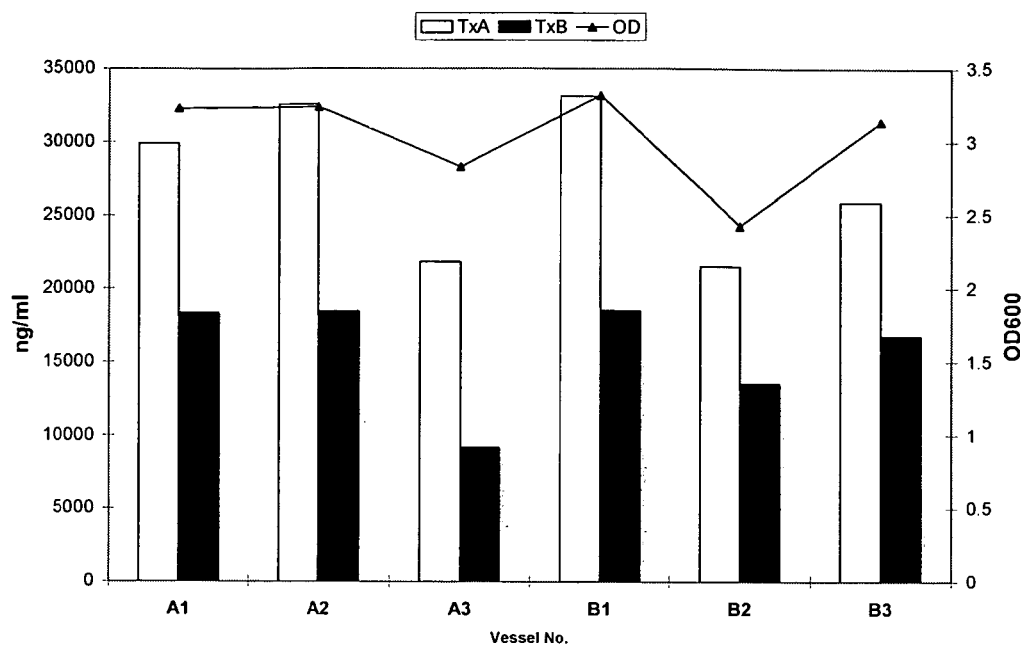
Fig. 9A: Toxin yields and cell growth at 18h
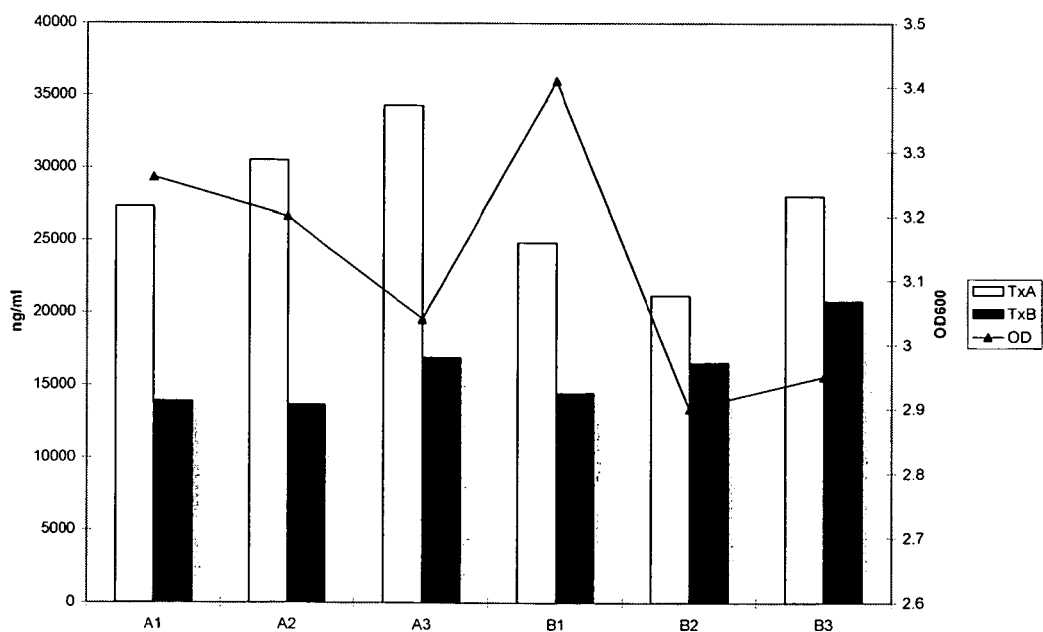
Fig. 9B: Toxin Yields and Cell Growth at 21h Fig. 10A: Toxin A Yield Fig. 10B: Toxin B Yield

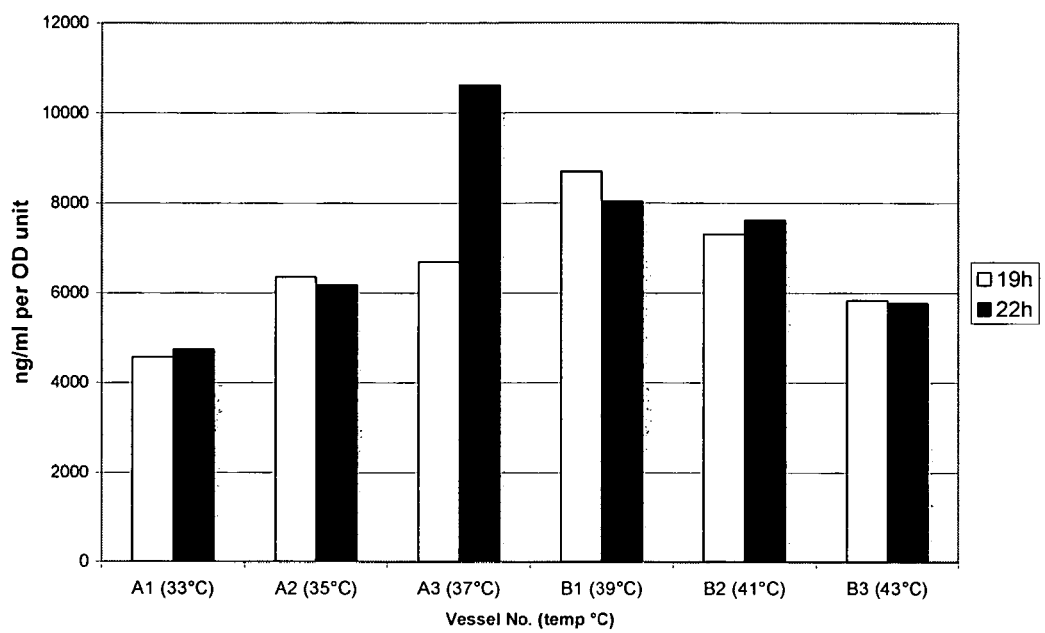
Fig. 10C: Specific Toxin A Productivity
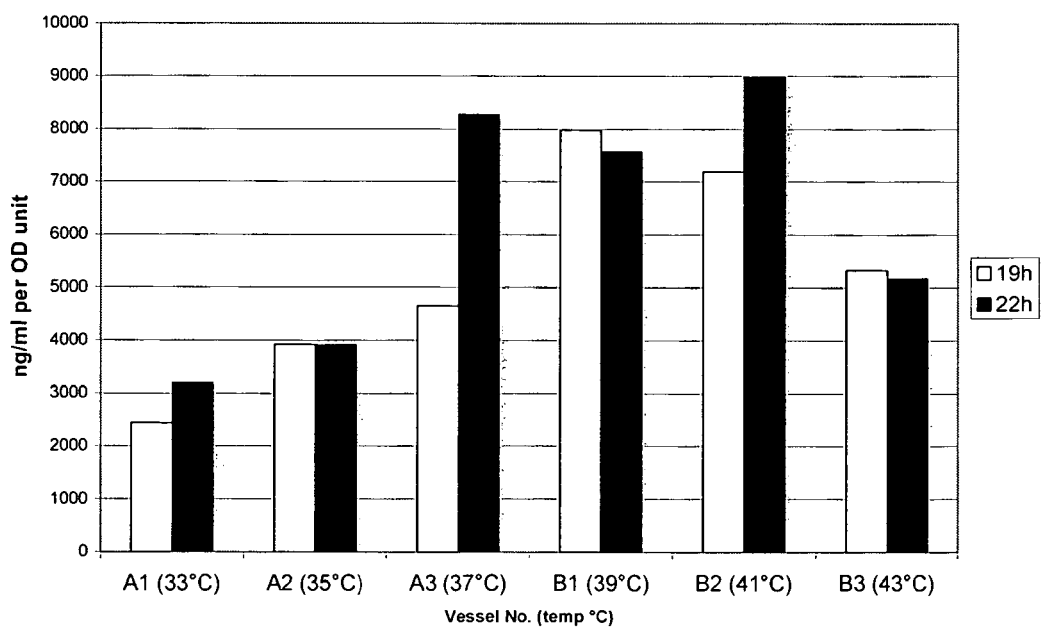
Fig. 10D: Specific Toxin B Productivity

METHODS AND COMPOSITIONS FOR INCREASING TOXIN PRODUCTION

CROSS-REFERENCE TO RELATED APPLICATIONS

This application is the U.S. national stage filing under 35 U.S.C. §371 of international application PCT/US2009/058268, filed Sep. 24, 2009, which claims benefit of Provisional Patent Application. 61/099,759, filed Sep. 24, 2008.

CROSS REFERENCE TO RELATED APPLICATIONS

This application claims priority from U.S. Provisional Patent Application No. 61/099,759, filed on Sep. 24, 2008, which is incorporated herein by reference in its entirety.

BACKGROUND OF THE INVENTION

*Clostridium difficile* (*C. difficile*) Toxins A and B are responsible for *C. difficile*-associated disease (CDAD), which manifests itself as nosocomial diarrhea and pseudomembranous colitis (Kuijper et al., Clinical Microbiology and Infection 12(Suppl. 6):2-18, 2006; Drudy et al., International Journal of Infectious Diseases 11(1):5-10, 2007; Warny et al., Lancet 366(9491):1079-1084, 2005; Dove et al., Infection and Immunity 58(2):480-488, 1990; Barroso et al., Nucleic Acids Research 18(13):4004, 1990).

Toxins A and B are encoded by two separate but closely linked (and highly homologous) genes. Toxins A and B are produced simultaneously in *C. difficile* strain VPI 10463 (ATCC 43255), and the ratio of the produced toxins is usually 3:1, respectively (Karlsson et al., Microbiology 145:1683-1693, 1999). The toxins begin to be formed during the exponential growth phase, and are usually released from the bacteria between 36 and 72 hours of culture. Toxins present within the bacteria can be released earlier by sonication or by use of a French pressure cell.

Treatment of the toxins with formaldehyde results in the corresponding Toxoids A and B, which are completely inactivated and retain at least partial immunogenicity (Torres et al., Infection and Immunity 63(12):4619-4627, 1995). It has been shown that vaccination employing both toxoids is effective in hamsters, healthy adults, and patients with recurrent CDAD (Torres et al., Infection and Immunity 63(12):4619-4627, 1995; Kotloff et al., Infection and Immunity 69(2):988-995, 2001; Sougioultzis et al., Gastroenterology 128(3):764-770, 2005; Tones et al., Vaccine Research 5(3):149-162, 1996). Additionally, the administration of both free and aluminum salt (adjuvant) bound toxoids leads to appropriate immune responses (Torres et al., Vaccine Research 5(3):149-162, 1996; Giannasca et al., Infection and Immunity 67(2):527-538, 1999).

The administration of both toxoids simultaneously is more effective than administration of the individual proteins alone (Kim et al., Infection and Immunity 55(12):2984-2992, 1987). A toxoid composition found effective in inducing protective immune responses against toxin A and toxin B in patients with recurrent CDAD included both toxoids, at a ratio of 1.5:1, A:B (Sougioultzis et al., Gastroenterology 128(3):764-770, 2005).

Both the A and B toxoids are thus candidates for vaccine development. Greater production efficiency of Toxins A and B is desired to facilitate vaccine production.

SUMMARY OF THE INVENTION

In one aspect, the invention features a culture medium (e.g., for culturing a *Clostridium difficile* bacterium) at a pH of between 6.35 and 7.45 (e.g., 6.5, 7.28, or between 6.35 and 6.65) including peptone (e.g., soy peptone), a yeast extract (e.g., Difco Bacto Yeast extract), a buffering agent (e.g., $NaHCO_3$), and a phosphate buffer (e.g., sodium phosphate, dibasic and potassium phosphate, monobasic). This culture medium can also include at least one additive (e.g., 2, 3, or more additives) selected from the group consisting of chromium trioxide, clindamycin, ascorbic acid, butyric acid, D(+)xylose, D-sorbitol, sucrose, and a combination of azaserine, adenosine, and biotin.

In another aspect, the invention features a bacterial culture including *Clostridium difficile* and culture medium including at least one additive (e.g., 2, 3, or more additives) selected from the group consisting of chromium trioxide, clindamycin, ascorbic acid, butyric acid, D(+)xylose, D-sorbitol, sucrose, and a combination of azaserine, adenosine, and biotin. This medium can also include peptone (e.g., soy peptone), yeast extract (e.g., Difco Bacto Yeast extract), sodium phosphate, dibasic, potassium phosphate, monobasic, and $NaHCO_3$, and the culture medium can be at a pH of between 6.35 and 7.45 (e.g., 6.5, 7.28, or between 6.35 and 6.65).

In another aspect, the invention features a method of culturing *Clostridium difficile* including inoculating culture medium with *Clostridium difficile*, with the medium including at least one additive (e.g., 2, 3, or more additives) selected from the group consisting of chromium trioxide, clindamycin, ascorbic acid, butyric acid, D(+)xylose, D-sorbitol, sucrose, and a combination of azaserine, adenosine, and biotin. This medium can also include peptone (e.g., soy peptone), yeast extract (e.g., Difco Bacto Yeast extract), sodium phosphate, dibasic, potassium phosphate, monobasic, and $NaHCO_3$, and the culture medium can be at a pH of between 6.35 and 7.45 (7.28 or between 6.35 and 6.65). Preferably the culture medium is at a pH of 6.5.

In another aspect, the invention features a method for obtaining or preparing one or more *C. difficile* toxins including by preparing an aqueous growth medium including soy peptone, inoculating the medium with a *C. difficile* bacterium (e.g., using an aqueous *C. difficile* culture), culturing the inoculated medium (e.g., at a pH of 6.5, 7.28, between 6.35 and 7.45, or between 6.35 and 6.65)) under conditions which facilitate growth of bacterium and toxin production (e.g., at a temperature between 37° C. to 41° C.), and isolating the one or more *C. difficile* toxins from growth medium (e.g., by removing from the growth medium viable *C. difficile* organisms and spores, separating the one or more toxins from the growth media, and purifying the one or more toxins). This culture medium can also include yeast extract, $NaHCO_3$, sodium phosphate, dibasic, potassium phosphate, monobasic, and D-sorbitol. This culturing can be carried out, e.g., under anaerobic conditions. The steps of inoculating the medium with a *C. difficile* bacterium (e.g., using an aqueous *C. difficile* culture) and culturing the inoculated medium can be repeated more than once, with inoculation into fresh growth medium with each repeat. This method can also include detoxifying the isolated one or more *C. difficile* toxins to prepare one or more toxoids (e.g., by reacting the one or more toxins by the addition of formaldehyde).

In another aspect, the invention features a method of enhancing the production of Toxin B from a *C. difficile* culture by preparing an aqueous growth medium including soy peptone, inoculating the medium with a *C. difficile* bacterium, culturing the inoculated medium at 37° C. to 41° C. and at a pH between pH 6.35 and pH 6.65 (e.g., at 37° C. and at a pH of 6.5). The pH and/or temperature can be held constant or vary during the culturing. The growth media can further include yeast extract, $NaHCO_3$; sodium phosphate, dibasic, potassium phosphate, monobasic, and D-sorbitol. Toxin B production can be enhanced relative to Toxin A production, producing, e.g., ratios of Toxin A relative to Toxin B of less than 3:1, 2:1, 1.5:1, or less.

In any of the foregoing aspects, yeast extract can be between 10 and 30 g/L, the $NaHCO_3$ can be between 2 and 5 g/L; the sodium phosphate, dibasic can be between 1 and 10 g/L, and the potassium phosphate, monobasic can be between 1 and 10 g/L. The adenosine can be present at a concentration of between 0.8 and 1.2 mM (e.g., 1 mM), the biotin at a concentration of between 40 and 60 nM (e.g., 50 nM), and the azaserine at a concentration between 15 and 50 µM (e.g., 50 µM). The concentration of D-sorbitol can be between 6 g/L and 20 g/L or between 8 g/L and 18 g/L (e.g., 12 g/L). The chromium trioxide can be present at a concentration of between 40 and 60 mg/L (e.g., 50 mg/L). The clindamycin can be present at a concentration between 0.4 and 0.6 mg/L (e.g., 0.5 mg/L). The ascorbic acid can be present at a concentration between 2.5 g/L and 10 g/L (e.g., 2.5 g/L and 10 g/L). The butyric acid can be present at a concentration between 30 mM and 60 mM (e.g., 30 mM and 60 mM). The D(+)xylose can be at a concentration between 6 g/L and 10 g/L (e.g., 6 g/L).

The invention provides several advantages. For example, the media and the methods of the invention allow increased production of *Clostridium difficile* toxins, which leads to increased efficiency and decreased costs in the production of toxin-based products such as vaccines. Other features and advantages of the invention will be apparent from the following Detailed Description, the Drawings, and the Claims.

BRIEF DESCRIPTION OF THE DRAWINGS

FIG. 3B is an SDS PAGE gel showing the amount of Toxin A produced in cells cultured with the indicated compounds at 24 hours.

FIG. 6A is a graph showing the amount of Toxin A produced (ng/ml) in cultures subject to the indicated pH control.

FIG. 6B is a graph showing the amount of Toxin B produced (ng/ml) in cultures subject to the indicated pH control.

FIG. 7A is a graph showing the amount of Toxin A produced (ng/ml) in cultures subject to the indicated pH control.

FIG. 7B is a graph showing the amount of Toxin B produced (ng/ml) in cultures subject to the indicated pH control.

FIG. 7C is a graph showing specific Toxin A productivity produced (ng/ml per OD unit) in the cultures subject to the indicated pH control.

FIG. 7D is a graph showing specific Toxin B productivity produced (ng/ml per OD unit) in the cultures subject to the indicated pH control.

FIG. 7E is a graph comparing the specific Toxin A and Toxin B produced (ng/ml) in cultures subject to the indicated pH control in Examples 6 and 7.

FIG. 8A is a graph showing the amount of Toxin A produced (ng/ml) in cultures subject to the indicated pH control and the indicated amount of sodium bicarbonate.

FIG. 8B is a graph showing the amount of Toxin B produced (ng/ml) in cultures subject to the indicated pH control and the indicated amount of sodium bicarbonate.

FIG. 9A is a graph showing the amounts of Toxin A and B produced (ng/ml) in 18 hour cultures subject to the indicated pH control in comparison to cell growth (OD600).

FIG. 9B is a graph showing the amounts of Toxin A and B produced (ng/ml) in 22 hour cultures subject to the indicated pH control in comparison to cell growth (OD600).

Figures 10A, 10B:
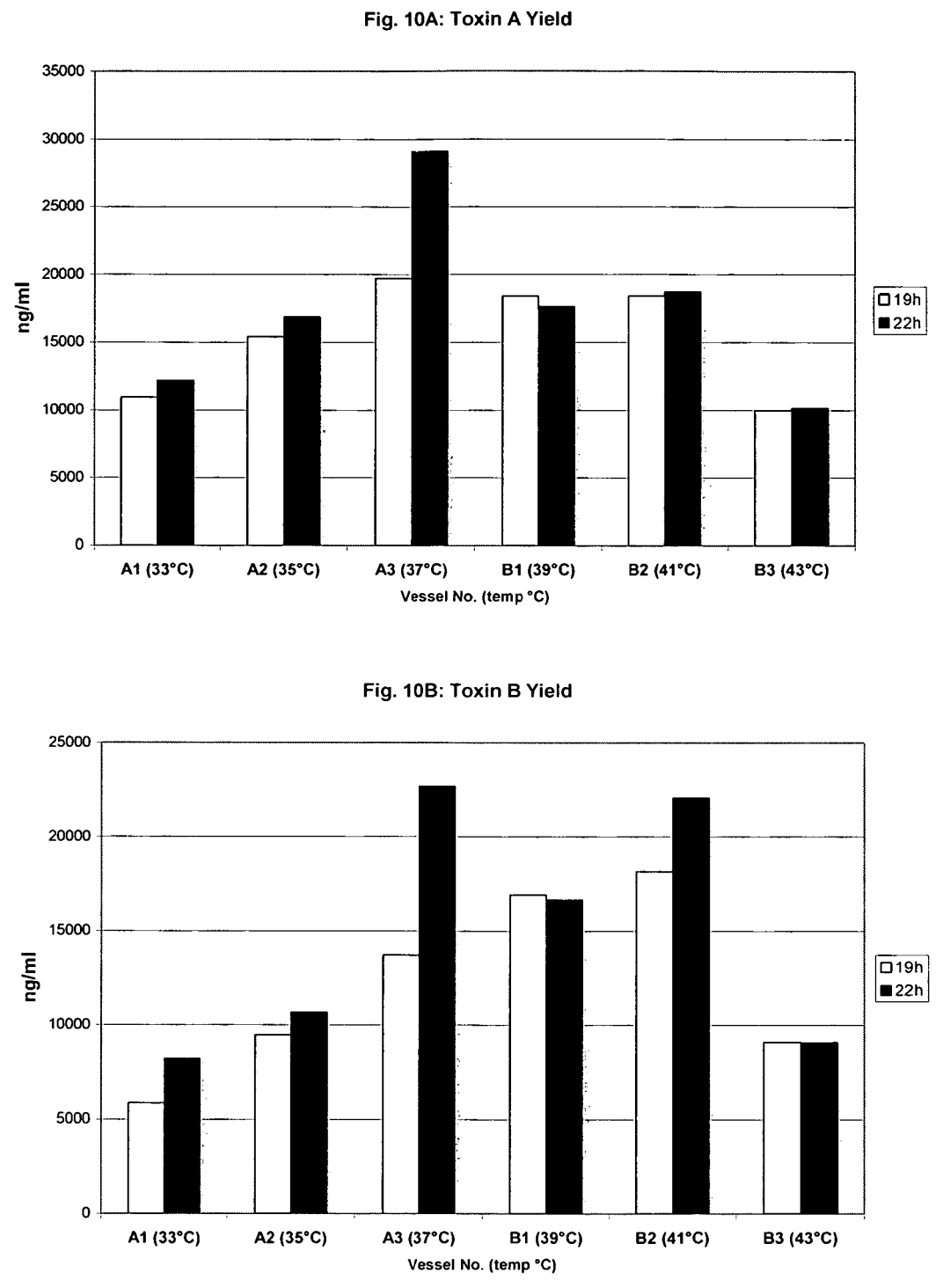

FIG. 10A is a graph showing the amount of Toxin A produced (ng/ml) in cultures subject to the indicated temperature.

FIG. 10B is a graph showing the amount of Toxin B produced (ng/ml) in cultures subject to the indicated temperature.

FIG. 10C is a graph showing specific Toxin A productivity produced (ng/ml per OD unit) in the cultures subject to the indicated temperature.

FIG. 10D is a graph showing specific Toxin B productivity produced (ng/ml per OD unit) in the cultures subject to the indicated temperature.

DETAILED DESCRIPTION

Figure 1A:
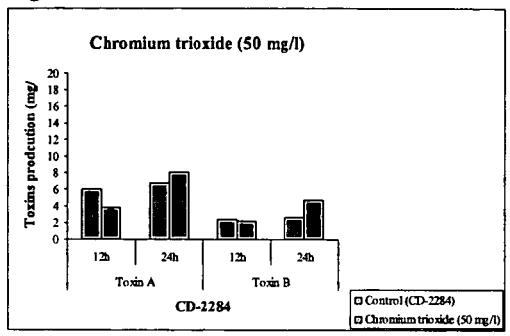
FIGS. 1A-G are graphs showing the amount of production of the indicated toxin in cultures containing the indicated additive at the indicated concentration.
Figure 1B:
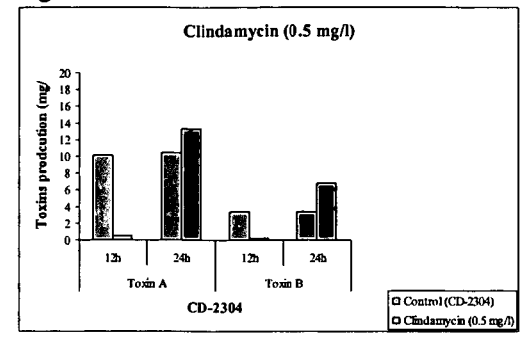
Figure 1C:
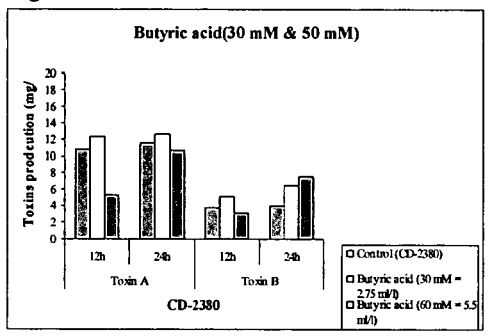
Figure 1D:
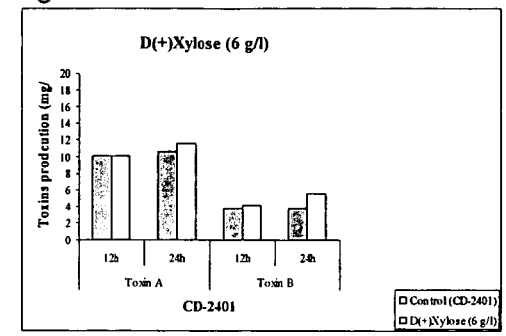
Figure 1E:
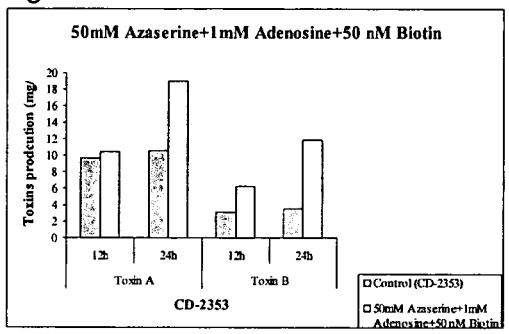
Figure 1F:
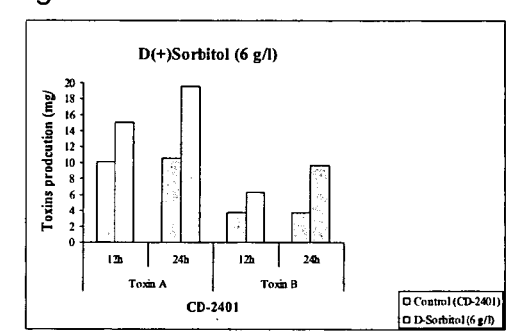
Figure 1G:
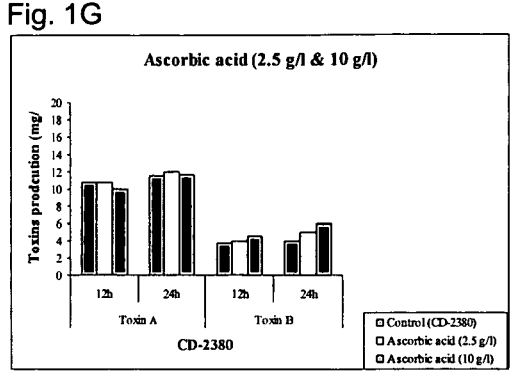

In general, the invention features methods and compositions (such as for example, culture media) for culturing *C. difficile* and producing the *C. difficile* Toxins A and B. These two toxins can be used individually or in combination, in the preparation of toxoids.

As discussed further below, the culturing of C. difficile in the media of the invention leads to enhanced Toxin A and Toxin B production. Similarly, as discussed further below, enhanced toxin production is seen by culturing C. difficile in accordance to the methods of the invention.

Basal Media

The compositions and methods of the invention feature the use of a basal medium in conjunction with certain medium additives. In one example, the basal medium is comprised of peptone (e.g., 20-40 g/L), yeast extract (e.g., 10-30 g/L), a phosphate buffer (such as for example, potassium phosphate monobasic (e.g., 0.5-1.5 g/L) and sodium phosphate dibasic (e.g., 1-10 g/L)) and a buffering agent (such as for example, sodium bicarbonate (e.g., 1-10 g/L)). The peptone used may be soy-based or animal-derived (such as for example, tryptone).

In one example, the basal medium is SYS media. SYS medium contains the ingredients listed in Table 1A at the indicated concentrations. The basal medium may be titrated to a pH of between 6.35 and 7.45 (for example, 6.5, 7.28, or between 6.35 and 6.65). Exemplary ranges of concentrations for each of the indicated ingredients are also indicated.

TABLE 1A

| Ingredient | Grams per liter | Acceptable range of grams per liter |
|---|---|---|
| Soy peptone A3 | 30 | 20-40 (e.g., 25-35 and 29-31) |
| Difco Bacto Yeast extracts | 20 | 10-30 (e.g., 15-25 and 19-21) |
| $KH_2PO_4$ | 0.9 | 0.5-1.5 (e.g., 0.8-1.0) |
| $Na_2HPO_4$ | 5 | 1-10 (e.g., 2-8 and 4-5) |
| $NaHCO_3$ | 5 | 1-10 (e.g., 2-8 and 4-5) |

Table 1B sets forth an alternative basal media useful in the compositions and methods of the invention, named TYS.

TABLE 1B

| Ingredient | Grams per liter | Acceptable range of grams per liter |
|---|---|---|
| Difco Bacto Tryptone | 30 | 20-40 (e.g., 25-35 and 29-31) |
| Difco Bacto Yeast extracts | 20 | 10-30 (e.g., 15-25 and 19-21) |
| $KH_2PO_4$ | 0.9 | 0.5-1.5 (e.g., 0.8-1.0) |
| $Na_2HPO_4$ | 5 | 1-10 (e.g., 2-8 and 4-5) |
| $NaHCO_3$ | 5 | 1-10 (e.g., 2-8 and 4-5) |

In substitution of the Soy peptone A3 and the Difco Bacto Tryptone any peptone (e.g., any soy peptone) can be utilized. Examples of soy peptones that can be used in the basal media (and their sources) include the following:

Kerry Biosciences: HyPer 1510,
IPS: Hy-Soy Kosher, and
Becton Dickinson: BD Select Phytone UF In substitution of the Difco Bacto Yeast Extract, any yeast extract can also be used in the basal media. Examples of suitable yeast extracts (and their sources) are readily known to those skilled the art.

The suitability of a particular peptone or yeast extract for use in the invention can be determined using the experimental methods described herein. The invention also includes use of other bacterial growth media, in combination with the additives described below.

Additives

The invention also features the use of certain additives with a basal media (e.g., SYS media). Exemplary additives of the invention are set forth in Table 2, which also includes the exemplary concentration ranges for the indicated additives, as well as a single exemplary concentration. Additives include:

Chromium trioxide (Chromium(VI) oxide $CrO_3$). Chromium trioxide is the acid anhydride of chromic acid. Chromium trioxide is a strong oxidant, highly toxic, corrosive, and carcinogenic compound.

Clindamycin ($C_{18}H_{33}ClN_2O_5S$). Clindamycin is a lincosamide antibiotic and is indicated for Clostridium difficile-associated diarrhea (the most frequent cause of pseudomembranous colitis). Clindamycin has a bacteriostatic effect. It interferes with bacterial protein synthesis by binding preferentially to the 50S subunit of the bacterial ribosome.

Azaserine ($C_5H_7N_3O_4$). Azaserine is a naturally occurring serine derivative diazo compound and is a known carcinogen. Azaserine is a glutamine analogue that irreversibly inhibits glutamine phosphoribosyl amidotransferase, which is involved in the biosynthesis of inosine monophosphate (IMP). IMP is an important precursor to the purine nucleotides which include adenosine monophosphate (AMP) and guanosine monophosphate (GMP).

Ascorbic acid ($C_6H_8O_6$). Ascorbic acid is a sugar acid with antioxidant properties. L-Ascorbic acid is also known as vitamin C.

Butyric acid ($C_4H_8O_2$). Butyric acid is a carboxylic acid and a short chain fatty acid. Butyric acid has been associated with the ability to inhibit the function of histone deacetylase enzymes, thereby favoring an acetylated state of histones in the cell.

Xylose ($C_5H_{10}O_5$). Xylose (wood sugar) is a five-carbon monosaccharide. Xylose can be metabolized into useful products by a variety of organisms, e.g., Clostridium difficile.

Sorbitol ($C_6H_{14}O_6$). Sorbitol, also known as glucitol, is a sugar alcohol. Sorbitol also is an osmotic stress agent (osmotic shock is induced by 0.5 M sorbitol).

TABLE 2

| Compounds (Concentration) | Concentration Range | | | | Single Concentration | | |
|---|---|---|---|---|---|---|---|
| Chromium trioxide | 40-60 mg/L | | | | 50 mg/L | | |
| Clindamycin | 0.1-10 mg/L (e.g., 0.4-0.6 mg/L) | | | | 0.5 mg/L | | |
| Azaserine, Adenosine, and Biotin | 15-50 µM | 0.5-1. mM (e.g., 0.8-1.2 mM) | 40-60 nM | 50 µM | 1 mM | 50 nM | |
| Ascorbic acid | 2.5-10 g/L | | | | 2.5 g/L | | |
| Butyric acid | 30-60 nM | | | | 60 mM | | |
| D(+)Xylose | 1-15 g/L (e.g., 6-10 g/L) | | | | 6 g/L | | |
| D-Sorbitol | 6-20 g/L (e.g., 8-18 g/L) | | | | 12 g/L | | |

Methods

Growth of *C. difficile* according to the methods of the invention proceeds in at least two phases: seed growth and fermentation. The seed growth phase, as described further below, may proceed in one or more seed culture stages (e.g., two stages or three stages).

A seed culture is first grown by inoculating seed medium with a sample from a stock culture (e.g., a working cell bank (WCB)). A sample of this seed culture is used either to inoculate a second seed culture or to inoculate a relatively large fermentation culture. Such seed cultures are typically carried out to allow the quantity of the microorganism from a stored culture (e.g., WCB) to be exponentially increased (scaled-up). Seed cultures can also be used to rejuvenate relatively dormant microbes in stored cultures. As is well understood in the art, more than one seed culture (e.g., two or three cultures or stages) can be used to scale-up the quantity of *C. difficile* for inoculation into the fermentation medium.

The number of seed cultures (or stages) used depends on, for example, the size and volume of the fermentation step. For example, the culture process may involve two seed cultures: a first seed culture is grown from an inoculation of a WCB (stage one seed culture), a sample of this seed culture is used to inoculate a second seed culture (stage two seed culture), and a sample from this second culture is used to inoculate a fermentation culture (fermentation stage). In a preferred embodiment of the present invention, the first and second seed cultures are grown in SYS media.

In stage one, a culture of *C. difficile* is suspended in seed medium and is incubated at a temperature between 30-40° C., preferably at 37±1° C., for 18 hours in an anaerobic environment. In stage two, a sample of the stage one seed medium is used to inoculate a stage two seed medium for further growth. After inoculation, the stage two medium is incubated at a temperature between 30-40° C., preferably at 37±1° C., for approximately 10 hours, also in an anaerobic environment. Preferably, growth in seed media at any stage does not result in cell lysis before inoculation of fermentation media. Additional growth in a third (fourth, etc.) stage seed culture can also be carried out.

In the fermentation stage, an appropriate concentration of seed culture, which can range from, e.g., 0.1-10%, is used to inoculate the fermentation media. Preferably, concentrations of 1.0% or 5.0% can be used. Most preferably, concentrations of 10% are used.

Fermentation is preferably carried out in an anaerobic chamber at approximately 35° C. to 45° C. and preferably at a temperature between 37° C. to 41° C. (e.g., 37° C.). The pH of the fermentation may be controlled at a pH between pH 6.35 to 7.45 (e.g., between 6.35 to 6.65, and preferably, at pH 6.5). Alternatively, the pH of the culture media is uncontrolled and is allowed to decrease naturally during the fermentation process.

*C. difficile* can be cultivated by fermentation with continuous exposure to a suitable gas or gas mixture (such as, for example, 80% nitrogen/10% $CO_2$/10% hydrogen, 100% $CO_2$, or 100% nitrogen). Such gases or gas mixtures may also be sparged (i.e., bubbled) through the medium during fermentation. As an alternative to sparging (or in addition to it), a gas mixture (e.g., 80% nitrogen/10% $CO_2$/10% hydrogen) or a gas (e.g., $CO_2$ or nitrogen) may be applied to the culture media as an overlay to degas the media throughout the fermentation process. The fermentation culture is preferably sparged prior to inoculation with either a mixture of 80% nitrogen/10% $CO_2$/10% hydrogen, 100% $CO_2$ or 100% nitrogen to remove any residual oxygen in the medium. During the fermentation process the culture may be sparged periodically. Alternatively, an overlay of a gas mixture or a gas (e.g., 100% nitrogen) may be applied to the culture.

Fermentation proceeds for approximately 16 to 24 hours (e.g., 18 to 21 hours). Preferably, agitation (e.g., 100 rpm) is applied to the culture medium during the fermentation process (and/or during stages one and two of seed cultures). Growth can be monitored by measuring the optical density (O.D.) of the medium.

*C. difficile* toxins can be isolated and purified from fermentation cultures using purification methods well known in the art such as for example, Kotloff et al., Infect. Immun 2001; 69:988-995, Coligan et al., "Current Protocols in Protein Science," Wiley & Sons; Ozutsumi et al., Appl. Environ. Microbiol. 49:939-943, 1985; and Kim et al., Infection and Immunity 55:2984-2992, 1987; which are incorporated herein by reference. The purified toxins can then, for example, be inactivated by chemical treatments known in the art (e.g., formaldehyde treatment).

All references cited within this disclosure are hereby incorporated by reference in their entirety. Certain embodiments are further described in the following examples. These embodiments are provided as examples only and are not intended to limit the scope of the claims in any way.

EXAMPLES

The basal media and additives of the invention were used to culture *Clostridium difficile* and produce *Clostridium difficile* Toxins A and B. Tables 3 and 4 (and FIGS. 1A-1G) summarize the amount of toxin produced by *Clostridium difficile* cells cultured in SYS media with the indicated additive at the indicated concentration after the indicated amount of time. Throughout the examples, *Clostridium difficile*, ATCC No. 43255, ATCC Lot# 2888434, was cultured.

TABLE 3

Percent increase in Toxins A and B at time points 12 and 24 hours following growth in the presence of the listed compounds

| Compounds | Toxin A | | Toxin B | |
|---|---|---|---|---|
| (Concentration) | 12 hrs. | 24 hrs. | 12 hrs. | 24 hrs. |
| Chromium trioxide (50 mg/L) | | 18.67 | | 80.45 |
| Clindamycin (0.5 mg/L) | | 27.52 | | 94.21 |
| 50 μM Azaserine + 1 mM Adenosine + 50 nM Biotin | 7.69 | 80.03 | 96.2 | 238.34 |
| Ascorbic acid (2.5 g/L) | | 4.65 | 5.26 | 24.42 |
| Ascorbic acid (10 g/L) | | 1.68 | 18.54 | 49.17 |
| Butyric acid (30 mM) | 13.8 | 10.07 | 33.6 | 60.95 |
| Butyric acid (60 mM) | | | | 88.6 |
| D(+)Xylose (6 g/L) | | 10.06 | 8.49 | 45.83 |
| D-Sorbitol (6 g/L) | 49.19 | 86.29 | 68.03 | 153.03 |

TABLE 4A

Total measured production of Toxins A and B at time points 12 and 24 hours following growth in the presence of the listed compounds

| Compounds | Toxin A (ng/mL) | | Toxin B (ng/mL) | |
|---|---|---|---|---|
| (Concentration) | 12 hrs. | 24 hrs. | 12 hrs. | 24 hrs. |
| Control (CD-2284) | 5974 | 6809 | 2436 | 2645 |
| Chromium trioxide (50 mg/L) | 3880 | 8080 | 2188 | 4773 |
| Increase (%) | | 18.67 | | 80.45 |
| Control (CD-2304) | 10083 | 10475 | 3392 | 3469 |
| Clindamycin (0.5 mg/L) | 611 | 13358 | 189 | 6737 |

TABLE 4A-continued

Total measured production of Toxins A and B at time points 12 and 24 hours following growth in the presence of the listed compounds

| Compounds (Concentration) | Toxin A (ng/mL) | | Toxin B (ng/mL) | |
|---|---|---|---|---|
| | 12 hrs. | 24 hrs. | 12 hrs. | 24 hrs. |
| Increase (%) | | 27.52 | | 94.21 |
| Control (CD-2353) | 9649 | 10554 | 3159 | 3529 |
| 50 µM Azaserine, 1 mM Adenosine, 50 nM Biotin | 10391 | 19000 | 6198 | 11940 |
| Increase (%) | 7.69 | 80.03 | 96.20 | 238.34 |
| Control (CD-2380) | 10822 | 11515 | 3825 | 3992 |
| Ascorbic acid (2.5 g/L) | 10789 | 12050 | 4026 | 4967 |
| Increase (%) | | 4.65 | 5.26 | 24.42 |
| Ascorbic acid (10 g/L) | 9957 | 11708 | 4534 | 5955 |
| Increase (%) | | 1.68 | 18.54 | 49.17 |
| Butyric acid (30 mM = 2.75 mL/l) | 12315 | 12674 | 5110 | 6425 |
| Increase (%) | 13.80 | 10.07 | 33.60 | 60.95 |
| Butyric acid (60 mM = 5.5 mL/l) | 5335 | 10681 | 3063 | 7529 |
| Increase (%) | | | | 88.60 |
| Control (CD-2401) | 10108 | 10508 | 3756 | 3832 |
| D(+)Xylose (6 g/L) | 10135 | 11565 | 4075 | 5588 |
| Increase (%) | | 10.06 | 8.49 | 45.83 |
| D-Sorbitol (6 g/L) | 15080 | 19575 | 6311 | 9696 |
| Increase (%) | 49.19 | 86.29 | 68.03 | 153.03 |

TABLE 4B

Total measured production of Toxins A and B at time points 12 and 24 hours following growth in the presence of the listed compounds

| Compounds (Concentration) | Toxin A (ng/mL) | | Toxin B (ng/mL) | |
|---|---|---|---|---|
| | 12 hrs. | 24 hrs. | 12 hrs. | 24 hrs. |
| 50 µM Azaserine + 1 mM Adenosine + 50 nM Biotin | 10391 | 19000 | 6198 | 11940 |
| 15 µM Azaserine + 1 mM Adenosine + 50 nM Biotin | 8525 | 10423 | 3430 | 3880 |
| 5 µM Azaserine + 1 mM Adenosine + 50 nM Biotin | 7471 | 7816 | 2665 | 2694 |

Example 1

This Example includes data on the amount of toxin produced when *Clostridium difficile* is cultured in SYS basal media in the absence and presence of various metallic ions.

Materials

The following are the Example 1 test compounds, along with the compound formula and source.

AFC-Ammonium ferric citrate ($C_6H_8O_7 \cdot nFe \cdot nH_3N$), USB Cat. 15751 Lot. 121753

FC-Ferric citrate ($C_6H_5FeO_7$), FW 244.95, MB Biomedicals LLC, Cat. 195181, Lot R23927

FG-Ferrous gluconate Hydrade ($C_{12}H_{22}FeO_{14}$)

FS-Ferric sulfate ($FeSO_4 \cdot 7H_2O$), FW 278.02 CA-Calcium chloride Anhydrous ($CaCl_2$), FW 110.98, J. T. Baker Cat. 1311-01, Lot. A13602

CC-Cobalt chloride 6 Hydrate Crystal ($CoCl_2 \cdot 6H_2O$), FW 237.93, Mallinckrodt Chemicals Cat. 4535-02

CT-Chromium trioxide Crystal ($CrO_3$), FW 99.99, J. T. Baker Cat. 1638-04, Lot.

MS-Magnesium sulfate ($MgSO_4 \cdot 7H_2O$), FW 246.50

MC-Manganese chloride ($MnCl_2 4H_2O$), FW 197.90, J. T. Baker Cat. 2540-04, Lot E37335

The following table indicates the natural pH of the indicated compound in solution at the indicated concentration.

| Compound solution 2 g/L | Natural pH | Compound solution 1 g/L | Natural pH |
|---|---|---|---|
| Ammonium ferric citrate | 5.0 | Calcium chloride | 4.7 |
| Ferric citrate | 3.0 | Cobalt chloride | 4.8 |
| Ferrous gluconate | 4.5 | Chromium trioxide | <2.5 |
| Ferric sulfate | 4.7 | Magnesium sulfate | 5.0 |
| | | Manganese chloride | 5.0 |

Methods

The following methods were used to test the production of Toxin A and B by *Clostridium difficile* when cultured in the presence of the above-listed additives.

I. Medium Preparations:
1. Prepare 1000 mL SYS medium in 2 L beaker.
2. Transfer SYS to media bottles and degas for over 30 minutes with 10% $H_2$ +10% $CO_2$ +80% $N_2$.
3. Before transferring the medium, fill gas (10% $H_2$ +10% $CO_2$ +80% $N_2$) from the fill port of the Flexboy bag into the bag to remove oxygen, then empty the gas from the bag. Connect the filling system manifold with the bags.
4. For seed medium in 50 mL Flexboy bags, pump 30 mL medium into the bag from the fill port with a flow speed at 100 mL/minute.
5. For fermentation medium in 250 mL Flexboy bags:
   i) Put the bag on a balance before filling with the medium and adjust to "0."
   ii) Pump the medium into the bag from the fill port with a flow speed at 100 mL/min until the balance show 50 g, stop the pumping.
6. Move the bag for seed-1 to 37° C. $CO_2$ incubator to warm overnight. Keep bag for seed-2 and fermentation at 4° C. until use.
7. Move the bags to 37° C. $CO_2$ incubator to warm up overnight before use.
8. For different compounds:
   i) Prepare 40 mL solutions of different compounds with the concentrations at 2.0 g/L (80 mg compound+40 mL di water (pH)).
   ii) Prepare 40 mL solutions of different compounds with the concentrations at 1.0 g/L (40 mg compound+40 mL di water (pH)).
   iii) For all compounds but ferric citrate, filter the solution using Millipore 50 mL disposable vacuum filtration system with 0.22 µm Millipore Express Plus membrane. The ferric citrate was autoclaved.
   iv) Before transfer of seed-2 to fermentation bags add the compound solutions as the following concentrations listed in the following table:

| Compounds (mg/L) | | Sterile di water (mL) | Total (mL) |
|---|---|---|---|
| | 2 g/L solution (mL) | | |
| Control (without any compound) | 0 | 2.5 | 2.5 |
| 100 mg/L (5 mg/50 mL) | 2.5 | 0 | 2.5 |
| | 1 g/L solution (mL) | | |
| 50 mg/L (2.5 mg/50 mL) | 2.5 | 0 | 2.5 |

II. Fermentation Process:
1. First stage seed culture: 1 mL WCB, containing 50% glycerol, was transferred into a 50 mL Flexboy bag containing 30 mL SYS medium and incubated at 37±1° C. for 24 hours.
2. Second stage seed culture: 1.5 mL of first stage seed culture at inoculums of 5% were transferred into the 50 mL Flexboy bag containing 30 mL SYS medium and incubated at 37±1° C. for 22 hours.
3. Fermentation: 2.5 mL of second stage seed culture was inoculated at 5% for each 250 mL Flexboy bag containing 50 mL of SYS medium and incubated at 37° C.±1° C. for 24 hours.
4. Take samples at 12 hours and 24 hours. Cell growth was measure at 600 nm. The blank of fermentation media was used as zero for the spectrophotometer. The cell concentration was diluted 10×.
5. The toxin production is measured by capture ELISA.

III. Capture ELISAs:
1. Toxin A standard Lot# CD-2062 (1072506A)
2. Goat anti-Toxin A, Lot# CD-2017
3. Mouse MAb to *C. difficile* Toxin A (PCG4)
4. Toxin B standard Lot#QC06329
5. Goat anti-Toxin B, Lot# C0210091
6. Mouse anti Toxin B Lot#030904

Results

1. The following table shows the amount of seed growth ($OD_{600\ nm}$) as measured by DU700.

| Seed-1 | Seed-2 |
| --- | --- |
| 1.73 | 2.31 |

2. The following table shows the amount of cell growth ($OD_{600\ nm}$) in cultures with the indicated compound.

| Test | 12 hours | 24 hours |
| --- | --- | --- |
| Control | 2.56 | 2.25 |
| Ammonium ferric citrate | 2.58 | 2.22* |
| Ferric citrate | 2.38 | 2.48* |
| Ferrous gluconate | 2.73 | 2.51* |
| Ferric sulfate | 2.55 | 2.73* |
| Calcium chloride | 2.39 | 2.20 |
| Cobalt chloride | 2.34 | 1.89* |
| Chromium trioxide | 1.48 | 1.02** |
| Magnesium sulfate | 2.37 | 2.03 |
| Manganese chloride | 2.52 | 1.97 |

Figure 2A:
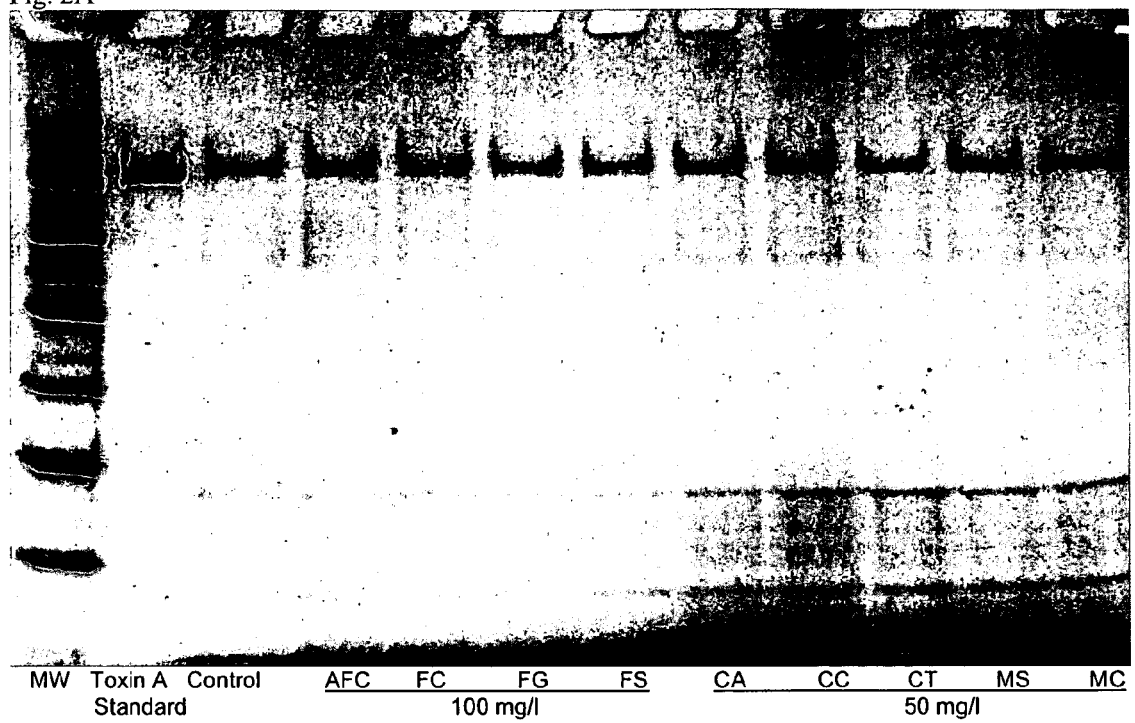
FIG. 2A is an SDS PAGE gel showing the amount of Toxin A produced in cells cultured with the indicated compounds at 12 hours.
Figure 2B:
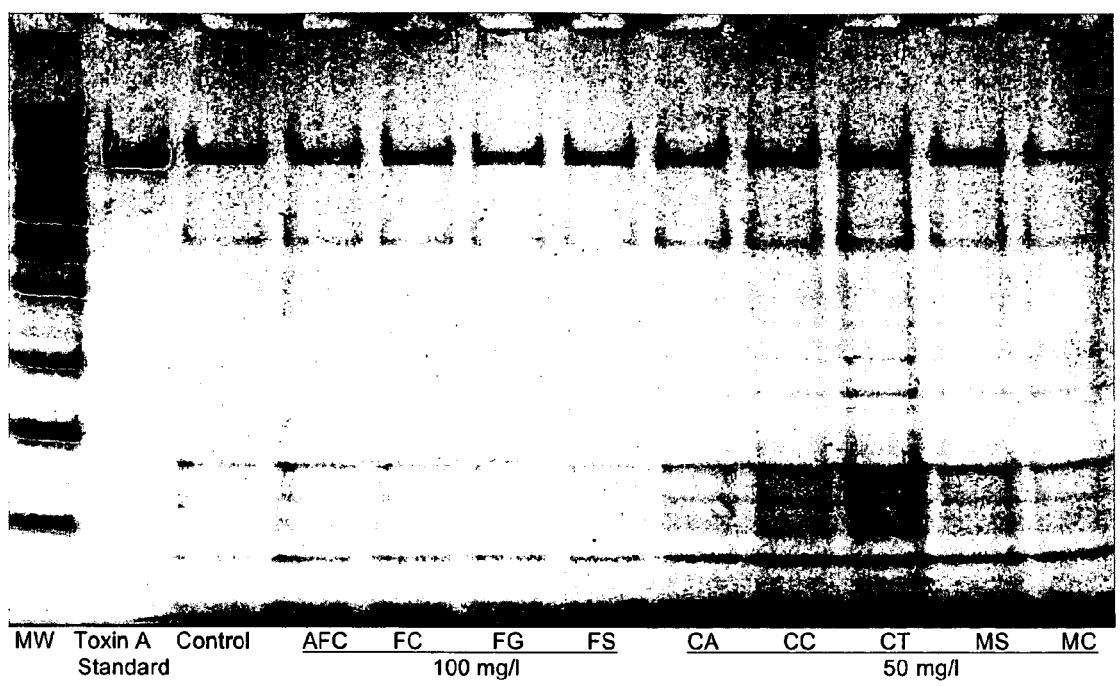
FIG. 2B is an SDS PAGE gel showing the amount of Toxin A produced in cells cultured with the indicated compounds at 24 hours.

*The broth became dark green because iron reacted with other compounds
**A lot of cells showed 3× to 5× longer than the normal cells in 24 h broth 3. The following table shows the amount of Toxin A produced (ng/mL) in cultures with the indicated compound (FIGS. 2A and 2B).

| Test | 12 hours | 24 hours |
| --- | --- | --- |
| Control | 5974 | 6809 |
| Ammonium ferric citrate | 5752 | 6634 |
| Ferric citrate | 5580 | 6544 |
| Ferrous gluconate | 5453 | 6208 |
| Ferric sulfate | 5162 | 5706 |
| Calcium chloride | 6294 | 6563 |
| Cobalt chloride | 5252 | 6647 |
| Chromium trioxide | 3880 | 8080 |
| Magnesium sulfate | 5060 | 5527 |
| Manganese chloride | 4768 | 5449 |

4. The following table shows the amount of Toxin B produced (ng/mL) in cultures with the indicated compound.

| Test | 12 hours | 24 hours |
| --- | --- | --- |
| Control | 2436 | 2645 |
| Ammonium ferric citrate | 2153 | 2503 |
| Ferric citrate | 2191 | 2550 |
| Ferrous gluconate | 2190 | 2082 |
| Ferric sulfate | 2068 | 2059 |
| Calcium chloride | 2494 | 2516 |
| Cobalt chloride | 2043 | 2721 |
| Chromium trioxide | 2188 | 4773 |
| Magnesium sulfate | 1873 | 1922 |
| Manganese chloride | 1784 | 1921 |

5. The following table shows the amount of spore formation in 24 hour fermentation in cultures with the indicated compound. Broth was examined by microscope.

| Test | 24 hours |
| --- | --- |
| Control | No spore formation found |
| Ammonium ferric citrate | No spore formation found |
| Ferric citrate | No spore formation found |
| Ferrous gluconate | No spore formation found |
| Ferric sulfate | No spore formation found |
| Calcium chloride | No spore formation found |
| Cobalt chloride | No spore formation found |
| Chromium trioxide | No spore formation found |
| Magnesium sulfate | No spore formation found |
| Manganese chloride | No spore formation found |

Conclusions

Chromium trioxide, when added to the SYS medium at 50 mg/L, caused increases in production of Toxin A (20%) and Toxin B (80%) after 24 hours in fermentation broth, but not after 12 hours in fermentation broth.

Example 2

This example includes data on the amount of toxin produced when *Clostridium difficile* is cultured in SYS basal media in the absence and presence of various antibiotics.

Materials

The following are antibiotics, along with the compound formula and source, which were tested in this example.

Cip-Ciprofloxacin ($C_{17}H_{18}FN_3O_3$) FW 331.35, Bio-Chemika, Lot#WA19781, soluble with 0.2 mL of 5 N HCl.

Cli-Clindamycin hydrochloride ($C_{18}H_{33}ClN_3O_5S \cdot HCl$) FW 461.44, Sigma C5269, Lot#37k1535, soluble in water.

Van-Vancomycin hydrochloride ($C_{66}H_{75}Cl_2N_9O_{24} \cdot HCl$) FW 1485, Sigma V20029, Lot#037K0686 soluble in water.

Pen G-Penicillin G Sodium salt ($C_{16}H_{17}N_2NaO_4S$) FW 356.4, Sigma P3032, Lot#057K04931, soluble in water.

Fe-EDTA was also tested (Ethylenediaminetetraacetic acid, Ferric Sodium Salt, ($C_{10}H_{12}FeN_2NaO_8$) FW 421.10, Acros Organics 304680050, Lot#A0245953).

Antibiotics were tested at the following concentrations:

Ciprofloxacin (2 mg/L and 10 mg/L), Clindamycin (0.5 mg/L and 2.5 mg/L), Vancomycin (0.1 mg/L and 0.5 mg/L), and Penicillin G (0.1 mg/L and 0.5 mg/L).

Ethylenediaminetetraacetic acid Ferric Sodium Salt was tested at a concentration of 100 mg/L.

Materials

The following materials were used to test the production of Toxin A and B by *Clostridium difficile* when cultured in the presence of the above antibiotics and compounds.

1. Make 100× concentration antibiotic solutions/10× Fe-EDTA solutions

| Antibiotics (mg/L) | Antibiotics powder (mg) | Sterile di water (mL) | 100× Concentration (mg/L) |
|---|---|---|---|
| Ciprofloxacin (10 mg/L) | 40 | 40 | 1000 |
| Clindamycin (2.5 mg/L) | 5 | 20 | 250 |
| Vancomycin (0.5 mg/L) | 2 | 40 | 50 |
| Penicillin G (0.5 mg/L) | 2 | 40 | 50 |

| Compounds (mg/L) | Compound (mg) | Sterile di water (mL) | 10× Concentration (mg/L) |
|---|---|---|---|
| Fe-EDTA 100 mg/L | 40 | 40 | 1000 |

2. Make 10× concentration of antibiotic solution:
   Take 4 mL of 100× concentration solution+36 mL di water.

Methods

I. Medium Preparations:
   1. Prepare 1000 mL SYS medium in 2 L beaker.
   2. Transfer SYS to media bottles and degas for over 30 minutes with 10% $H_2$+10% $CO_2$+80% $N_2$.
   3. Before transferring the medium, fill gas (10% $H_2$+10% $CO_2$+80% $N_2$) from the fill port of the Flexboy bag into the bag to remove oxygen, then empty the gas from the bag. Connect the filling system manifold with the bags.
   4. For seed medium in 50 mL Flexboy bags, pump 30 mL medium into the bag from the fill port with a flow speed at 100 mL/minute.
   5. For fermentation medium in 250 mL Flexboy bags:
      i) Put the bag on a balance before filling with the medium and adjust to "0".
      ii) Pump the medium into the bag from the fill port with a flow speed at 100 mL/min until the balance show 50 g, stop the pumping.
   6. Move the bag for seed-1 to 37° C. $CO_2$ incubator to warm overnight. Keep bag for seed-2 and fermentation at 4° C. until use.
   7. Move the bags to 37° C. $CO_2$ incubator to warm up overnight before use.
   8. For different antibiotics:
      i) Prepare 40 mL solutions of different antibiotics with the concentrations at 10× (see above table).
      ii) Prepare 40 mL solutions of FE-EDTA with the concentrations at 1000 mg/L (40 mg compound+40 mL di water (pH)).
      iii) Filter the solution using the Millipore 50 mL Disposable Vacuum Filtration System with 0.22 μm Millipore Express Plus Membrane.
      iv) Before transfer of seed-2 to fermentation bags, add the compound solutions at the following concentrations listed in the following tables.

| | 10× Solution (mL) | Sterile di water (mL) | Total (mL) |
|---|---|---|---|
| Antibiotics (mg/L) | | | |
| Control (without antibiotics) | 0 | 5 | 5 |
| Ciprofloxacin 2 mg/L (100 μg/50 mL) | 1 | 4 | 5 |
| Ciprofloxacin 10 mg/L (500 μg/50 mL) | 5 | 0 | 5 |
| Clindamycin 0.5 mg/L (25 μg/50 mL) | 1 | 4 | 5 |
| Clindamycin 2.5 mg/L (125 μg/50 mL) | 5 | 0 | 5 |
| Vancomycin 0.1 mg/L (5 μg/50 mL) | 1 | 4 | 5 |
| Vancomycin 0.5 mg/L (25 μg/50 mL) | 5 | 0 | 5 |
| Penicillin G 0.1 mg/L (5 μg/50 mL) | 1 | 4 | 5 |
| Penicillin G 0.5 mg/L (25 μg/50 mL) | 5 | 0 | 5 |
| Compounds (mg/L) | | | |
| Fe-EDTA 100 mg/L (5 mg/50 mL) | 5 | 0 | 5 |

II. Fermentation Process:
   1. First stage seed culture: 1 mL WCB, containing 50% glycerol, was transferred into a 50 mL Flexboy bag containing 30 mL SYS medium and incubated at 37±1° C. for 24 hours.
   2. Second stage seed culture: 1.5 mL of first stage seed culture at inoculums of 5% were transferred into the 50 mL Flexboy bag containing 30 mL SYS medium and incubated at 37±1° C. for 22 hours.
   3. Fermentation: 2.5 mL of second stage seed culture was inoculated at 5% for each 250 mL Flexboy bag containing 50 mL of SYS medium and incubated at 37° C.±1° C. for 24 hours.
   4. Take samples at 12 hours and 24 hours. Cell growth was measure at 600 nm. The blank of fermentation media was used as zero for the spectrophotometer. The cell concentration was diluted 10×.
   5. The toxin production is measured by capture ELISA.

III. Capture ELISAs:
   1. Toxin A standard Lot# CD-2062 (1072506A)
   2. Goat anti-Toxin A, Lot# CD-2017
   3. Mouse MAb to *C. difficile* Toxin A (PCG4)
   4. Toxin B standard Lot#QC06329
   5. Goat anti-Toxin B, Lot# C0210091
   6. Mouse anti Toxin B Lot#030904

Results

1. The following table shows the amount of seed growth ($OD_{600\ nm}$) as measured by DU700.

| Seed-1 | Seed-2 |
|---|---|
| 2.32 | 2.82 |

2. The following table shows the amount of cell growth ($OD_{600\ nm}$) in cultures with the indicated compound.

| Test | | mg/L | 12 hours | 24 hours |
|---|---|---|---|---|
| Control | | — | 2.71 | 2.48 |
| Ciprofloxacin | | 2 | 2.60 | 2.53 |
| | | 10 | 0.87 | 1.38 |
| Clindamycin | | 0.5 | 1.24 | 2.53 |
| | | 2.5 | 0.11 | 0.75 |
| Vancomycin | | 0.1 | 3.01 | 2.53 |
| | | 0.5 | 3.08 | 2.52 |
| Penicillin G | | 0.1 | 2.69 | 2.49 |
| | | 0.5 | 2.64 | 2.79 |
| Fe-EDTA | | 100 | 2.91 | 2.37 |

Figure 3A:
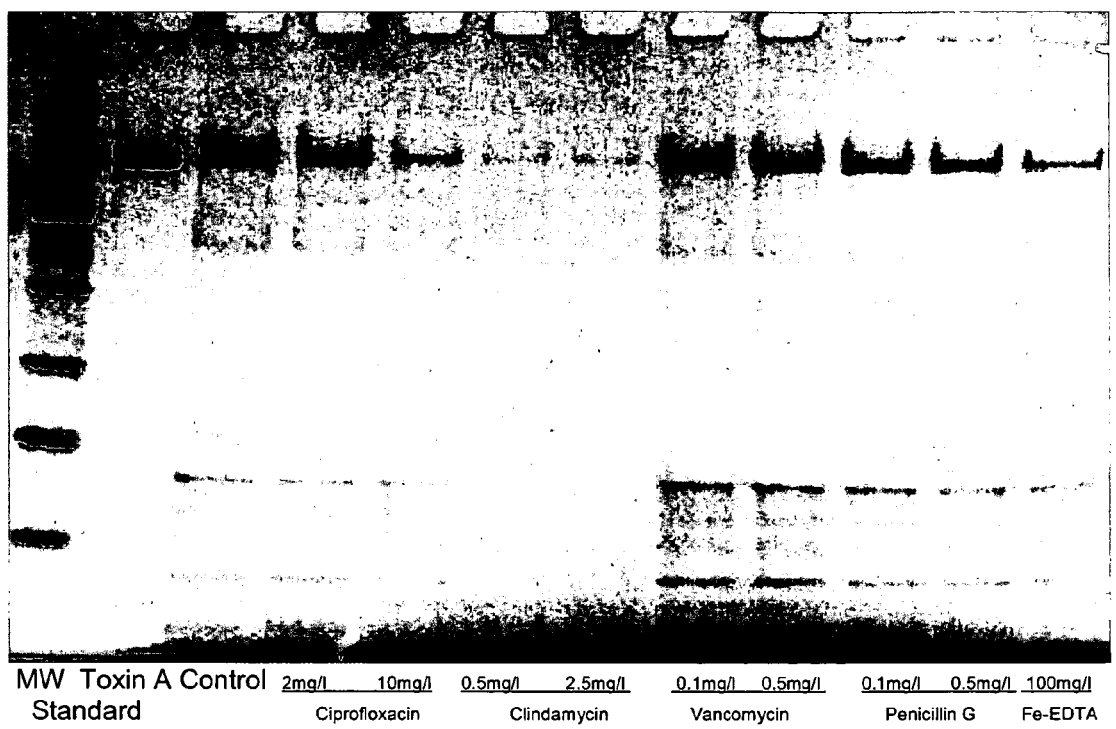
FIG. 3A is an SDS PAGE gel showing the amount of Toxin A produced in cells cultured with the indicated compounds at 12 hours.

3. The following table shows the amount of Toxin A produced (ng/mL) in cultures with the indicated compound (FIGS. 3A and 3B).

| Test | mg/L | 12 hours | 24 hours |
|---|---|---|---|
| Control | — | 10083 | 10475 |
| Ciprofloxacin | 2 | 6309 | 6953 |
|  | 10 | 1685 | 8614 |
| Clindamycin | 0.5 | 611 | 13358 |
|  | 2.5 | 496 | 445 |
| Vancomycin | 0.1 | 9142 | 9557 |
|  | 0.5 | 8328 | 9305 |
| Penicillin G | 0.1 | 8435 | 8871 |
|  | 0.5 | 8142 | 8746 |
| Fe-EDTA | 100 | 7256 | 8485 |

4. The following table shows the amount of Toxin B produced (ng/mL) in cultures with the indicated compound.

| Test | mg/L | 12 hours | 24 hours |
|---|---|---|---|
| Control | — | 3392 | 3469 |
| Ciprofloxacin | 2 | 2135 | 2112 |
|  | 10 | 707 | 3448 |
| Clindamycin | 0.5 | 189 | 6737 |
|  | 2.5 | 146 | 131 |
| Vancomycin | 0.1 | 3131 | 3216 |
|  | 0.5 | 2770 | 3127 |
| Penicillin G | 0.1 | 2755 | 3133 |
|  | 0.5 | 2816 | 2664 |
| Fe-EDTA | 100 | 2427 | 2541 |

5. The following table indicates cell morphological characteristics in cultures with the indicated compound.

| Test | mg/L | 12 hours |
|---|---|---|
| Control | — | Normal |
| Ciprofloxacin | 2 | Normal |
|  | 10 | Many cells were 2-4× longer than normal cells. Some cells were curved. |
| Clindamycin | 0.5 | Normal |
|  | 2.5 | Most sizes of the cells were 2× smaller than normal. Cells grow very slow |
| Vancomycin | 0.1 | Some cells were 2× longer than normal cells |
|  | 0.5 | Some cells were 2× longer than normal cells |
| Penicillin G | 0.1 | Normal |
|  | 0.5 | Normal |
| Fe-EDTA | 100 | Normal |

6. The following table shows the amount of spore formation in 24 h fermentation in cultures with the indicated compound. Broth was examined by microscope.

| Test | mg/L | 24 hours |
|---|---|---|
| Control | — | No spore formation found |
| Ciprofloxacin | 2 | No spore formation found |
|  | 10 | No spore formation found |
| Clindamycin | 0.5 | No spore formation found |
|  | 2.5 | No spore formation found |
| Vancomycin | 0.1 | No spore formation found |
|  | 0.5 | No spore formation found |
| Penicillin G | 0.1 | No spore formation found |
|  | 0.5 | No spore formation found |
| Fe-EDTA | 100 | No spore formation found |

Conclusions

Clindamycin, when added to SYS medium at 0.5 mg/L, caused increases in Toxin A (28%) and Toxin B (94%) after 24 hours in fermentation broth, but not after 12 hours in fermentation broth.

Example 3

This Example includes data on the amount of toxin produced when *Clostridium difficile* is cultured in SYS basal media in the absence and presence of various vitamins and antibiotics The following are the Example 3 test compounds, along with the compound formula and source.

Aza-Azaserine ($C_5H_7N_3O_4$) FW 173.10, (O-diaxoacetyl-L-serine) Fluka BioChemika, 11430 Lot#1301321, soluble in water.

Ade-Adenosine ($C_{10}H_{13}N_5O_4$) FW 267.25, Sigma A4036, Lot#046K06612, soluble with 5N HCl.

$B_{12}$-Vitamin $B_{12}$ ($C_{63}H_{88}CoN_{14}O_{14}P$) FW 1,355.37, Sigma, V6629Lot#124K17072, soluble in water.

Bio-d-Biotin ($C_{10}H_{16}N_2O_3S$) FW 244, Supelco 4-7868, Lot#LB5668 soluble with 5N HCl.

The following combinations of compounds were also tested at the indicated concentrations.

1-50 μM Azaserine (8650 μg/L)+1 mM Adenosine (267 mg/L)+50 nM Biotin (12.2 μg/L)

50 μM Azaserine (432.5 μg/50 mL)+1 mM Adenosine (13.35 mg/50 mL)+50 nM Biotin (610 ng/50 mL)

2-15 μM Azaserine (2595 μg/L)+1 mM Adenosine (267 mg/L)+50 nM Biotin (12.2 μg/L)

15 μM Azaserine (129.75 μg/50 mL)+1 mM Adenosine (13.35 mg/50 mL)+50 nM Biotin (610 ng/50 mL)

3-15 μM Azaserine (2595 μg/L), (129.75 μg/50 m/l)

4-5 μM Azaserine (865 μg/L)+1 mM Adenosine (267 mg/L)+50 nM Biotin (12.2 μg/L)

5 μM Azaserine (43.25 μg/50 mL)+1 mM Adenosine (13.35 mg/50 mL)+50 nM Biotin (610 ng/50 mL)

5-5 μM Azaserine (865 μg/L)+1 mM Adenosine (267 mg/L)+50 μM Biotin (12.2 ng/L)

5 μM Azaserine (43.25 μg/50 mL)+1 mM Adenosine (13.35 mg/50 mL)+50 μM Biotin (0.61 ng/50 mL)

6-0.05 nM d-Biotin (12.2 ng/L), (0.61 ng/50 mL)

7-0.5 nM d-Biotin (122 ng/L), (6.1 ng/50 mL)

8-5 nM d-Biotin (1.22 μg/L), (61 ng/50 mL)

9-50 nM Vitamin B12 (67.77 μg/L), (3.39 μg/50 mL)

Materials

1. Make 50× concentration solutions.

| Test component | Chemical (mg) | Sterile di water (mL) | 50× Concentration (mg/L) |
|---|---|---|---|
| Azaserine (50 μM = 8.65 mg/L) | 4.325 | 10 | 432.5 (2.5 mM) |
| Adenosine (1 mM = 267 mg/L) | 133.5 | 10 | 13350 (50 mM) |

| Test component | 2.5 mM Aza (mL) | Sterile di water (mL) | 250 μM Azaserine (mL) |
|---|---|---|---|
| Azaserine (5 μM = 865 μg/L) | 2 | 18 | 20 |

2. Make d-Biotin (500 µM) solutions, then dilute to 2.5 µM, 50 nM, 5 nM, and 0.5 nM.

| Test component | d-Biotin (mg) | Sterile di water (mL) | 500 µM d-Biotin (mg/L) |
|---|---|---|---|
| d-Biotin (50 nM = 12.2 µg/L) | 2.44 | 20 | 122 |

3. Make 50× concentration solutions then dilute to 10×.

| Test component | Vitamin B12 (mg) | Sterile di water (mL) | 50× Concentration (mg/L) |
|---|---|---|---|
| Vitamin B12 (50 nM = 67.8 mg/L) | 33.9 | 10 | 3390 (2.5 µM) |

| Test component | 50× concentration (mL) | Sterile di water (mL) | 10× Concentration (mg/L) |
|---|---|---|---|
| Vitamin B12 (50 nM = 67.8 mg/L) | 2 | 8 | 678 (500 nM) |

Methods

I. Medium Preparations:
  1. Prepare 1000 mL SYS medium in 2 L beaker.
  2. Transfer SYS to media bottles and degas for over 30 minutes with 10% $H_2$+10% $CO_2$+80% $N_2$.
  3. Before transferring the medium, fill gas (10% $H_2$+10% $CO_2$+80% $N_2$) from the fill port of the Flexboy bag into the bag to remove oxygen, then empty the gas from the bag. Connect the filling system manifold with the bags.
  4. For seed medium in 50 mL Flexboy bags, pump 30 mL medium into the bag from the fill port with a flow speed at 100 mL/minute.
  5. For fermentation medium in 250 mL Flexboy bags:
     i) Put the bag on a balance before filling with the medium and adjust to "0."
     ii) Pump the medium into the bag from the fill port with a flow speed at 100 mL/minute until the balance show 50 g, stop the pumping.
  6. Move the bag for seed-1 to 37° C. $CO_2$ incubator to warm overnight. Keep bag for seed-2 and fermentation at 4° C. until use.
  7. Move the bags to 37° C. $CO_2$ incubator to warm up overnight before use.
  8. For different compounds:
     i) Prepare the solutions (see above table).
     ii) Filter the solution using the Millipore 50 mL Disposable Vacuum Filtration System with 0.22 µm Millipore Express Plus Membrane.
     iii) Before transfer of seed-2 to fermentation bags, add the compound solutions as the following concentrations listed in the following tables.

| Chemical add to 50 mL SYS medium | 2.5 mM Aza (mL) | 50 mM Ade (mL) | 2.5 µM Bio (mL) | di water (mL) | Total (mL) |
|---|---|---|---|---|---|
| Control | 0 | 0 | 0 | 5 | 5 |
| #1-50 µM Azaserine + 1 mM Adenosine + 50 nM Biotin | 1 | 1 | 1 | 2 | 5 |

-continued

| | 250 µM Aza (mL) | 50 mM Ade (mL) | 2.5 µM Bio (mL) | di water (mL) | Total (mL) |
|---|---|---|---|---|---|
| #2-15 µM Azaserine + 1 mM Adenosine + 50 nM Biotin | 3 | 1 | 1 | 0 | 5 |
| #3-15 µM Azaserine | 3 | 0 | 0 | 2 | 5 |
| #4-5 µM Azaserine + 1 mM Adenosine + 50 nM Biotin | 1 | 1 | 1 | 2 | 5 |

| | 50 µM Aza (mL) | 50 mM Ade (mL) | 5 nM Bio (mL) | di water (mL) | Total (mL) |
|---|---|---|---|---|---|
| #5-5 µM Azaserine + 1 mM Adenosine + 50 pM Biotin) | 1 | 1 | 0.5 | 2.5 | 5 |

| | 0.5 nM Biotin (mL) | 5 nM Biotin (mL) | 50 nM Biotin (mL) | Total (mL) |
|---|---|---|---|---|
| #6-0.05 nM Biotin | 5 | 0 | 0 | 5 |
| #7-0.5 nM Biotin | 0 | 5 | 0 | 5 |
| #8-5 nM Biotin | 0 | 0 | 5 | 5 |

| | 500 nM Vitamin B12 (mL) | Total (mL) |
|---|---|---|
| #9-50 nM Vitamin B12 (67.77 µg/L) | 5 | 5 |

II. Fermentation Process:
  1. First stage seed culture: 1 mL WCB, containing 50% glycerol, was transferred into a 50 mL Flexboy bag containing 30 mL SYS medium and incubated at 37±1° C. for 24 hours.
  2. Second stage seed culture: 1.5 mL of first stage seed culture at inoculums of 5% were transferred into the 50 mL Flexboy bag containing 30 mL SYS medium and incubated at 37±1° C. for 22 hours.
  3. Fermentation: 2.5 mL of second stage seed culture was inoculated at 5% for each 250 mL Flexboy bag containing 50 mL of SYS medium and incubated at 37° C.±1° C. for 24 hrs.
  4. Take samples at 12 hours and 24 hours. Cell growth was measure at 600 nm. The blank of fermentation media was used as zero for the spectrophotometer. The cell concentration was diluted 10×.
  5. The toxin production is measured by capture ELISA.

III. Capture ELISAs:
  1. Toxin A standard Lot# CD-2062 (1072506A)
  2. Goat anti-Toxin A, Lot# CD-2017
  3. Mouse MAb to *C. difficile* Toxin A (PCG4)
  4. Toxin B standard Lot#QC06329
  5. Goat anti-Toxin B, Lot# C0210091
  6. Mouse anti Toxin B Lot#030904

Results

1. The following table shows the amount of seed growth ($OD_{600\ nm}$) as measured by DU700.

| Seed-1 | Seed-2 |
|---|---|
| 2.53 | 2.49 |

2. The following table shows the amount of cell growth ($OD_{600\ nm}$) in cultures with the indicated compound.

| Test | 12 hours | 24 hours |
|---|---|---|
| Control | 2.71 | 2.39 |
| #1-50 μM Azaserine + 1 mM Adenosine + 50 nM Biotin | 1.19 | 0.42 |
| #2-15 μM Azaserine + 1 mM Adenosine + 50 nM Biotin | 2.76 | 2.02 |
| #3-15 μM Azaserine | 2.33 | 2.55 |
| #4-5 μM Azaserine + 1 mM Adenosine + 50 nM Biotin | 2.84 | 2.48 |
| #5-5 μM Azaserine + 1 mM Adenosine + 50 pM Biotin | 2.49 | 2.47 |
| #6 0.05 nM Biotin | 3.03 | 2.74 |
| #7 0.5 nM Biotin | 2.59 | 2.51 |
| #8 5 nM Biotin | 2.86 | 2.54 |
| #9 50 nM Vitamin B12 | 2.82 | 2.88 |

3. The following table shows the amount of Toxin A produced (ng/mL) in cultures with the indicated compound.

| Test | 12 hours | 24 hours |
|---|---|---|
| Control | 9649 | 10554 |
| #1-50 μM Azaserine + 1 mM Adenosine + 50 nM Biotin | 10391 | 19000 |
| #2-15 μM Azaserine + 1 mM Adenosine + 50 nM Biotin | 8525 | 10423 |
| #3-15 μM Azaserine | 9333 | 10838 |
| #4-5 μM Azaserine + 1 mM Adenosine + 50 nM Biotin | 7471 | 7816 |
| #5-5 μM Azaserine + 1 mM Adenosine + 50 pM Biotin | 9933 | 10811 |
| #6 0.05 nM Biotin | 8708 | 9481 |
| #7 0.5 nM Biotin | 8601 | 9124 |
| #8 5 nM Biotin | 8573 | 8877 |
| #9 50 nM Vitamin B12 | 5858 | 6286 |

4. The following table shows the amount of Toxin B produced (ng/mL) in cultures with the indicated compound.

| Test | 12 hours | 24 hours |
|---|---|---|
| Control | 3159 | 3529 |
| #1-50 μM Azaserine + 1 mM Adenosine + 50 nM Biotin | 6198 | 11940 |
| #2-15 μM Azaserine + 1 mM Adenosine + 50 nM Biotin | 3430 | 3880 |
| #3-15 μM Azaserine | 3589 | 4112 |
| #4-5 μM Azaserine + 1 mM Adenosine + 50 nM Biotin | 2665 | 2694 |
| #5-5 μM Azaserine + 1 mM Adenosine + 50 pM Biotin | 3345 | 3813 |
| #6 0.05 nM Biotin | 2616 | 3167 |
| #7 0.5 nM Biotin | 2717 | 3084 |
| #8 5 nM Biotin | 2756 | 2936 |
| #9 50 nM Vitamin B12 | 1819 | 2030 |

Conclusions

50 μM Azaserine, 1 mM Adenosine, and 50 nM Biotin together, when added to the SYS medium, caused increases in production of Toxin A (80%) and Toxin B (238%) after 24 hours in fermentation broth.

Example 4

This Example includes data on the amount of toxin produced when *Clostridium difficile* is cultured in SYS basal media in the absence and presence of various amino acids and organic compounds.

Materials

The following are the Example 4 test compounds, along with the compound formula and source.

Arg-L-Arginine Monohydrochloride ($C_6H_4N_4O_2 \cdot HCl$), FW. 210.67 Sigma A5131-500G, Lot# 016K0001, soluble in water.

Cys-L-Cysteine ($C_3H_7NO_2S$), FW 121.16, Sigma C-7352, Lot#082K0377, soluble in water.

Tyr-L-Tyrosine ($C_9H_{11}NO_3$), FW 181.19, Sigma T8566, Lot#107K0157, soluble in water with HCl.

Asc-Ascorbic acid ($C_6H_8O_6$) FW 176.12, Sigma A5960 Lot#043K0131, soluble in water.

But-Butyric acid ($C_4H_8O_2$) FW 88.11, Aldrich B103500 Lot#03511DA, soluble in water.

These compounds were tested using the following concentrations (10×):

L-Arginine Monohydrochloride (50 mM).
L-Tyrosine (50 mg/L).
L-Cysteine (0.33 mM, 10 mM, and 33 mM).
Ascorbic acid (2.5 g/L and 10 g/L).
Butyric acid (30 mM and 60 mM).

1. Make 10× Arginine solutions.

| Test component | Arginine (g) | Sterile di water (mL) | 10× Concentration (g/L) |
|---|---|---|---|
| Arginine (50 mM = 10.5 g/L) | 4.2 | 40 | 105 |

2. Make 10× Cysteine solutions at 33 mM then dilute to 1 mM and 0.33 mM.

| Test component | Cysteine (g) | Sterile di water (mL) | 10× Concentration (g/L) |
|---|---|---|---|
| Cysteine (33 mM = 4 g/L) | 1.6 | 40 | 40 |

| Test component | 10× 33 mM Cys. (mL) | Sterile di water (mL) | 10× Concentration (g/L) |
|---|---|---|---|
| Cysteine (3.3 mM = 400 mg/L) | 4 | 36 | 4 |

| Test component | 10× 3.3 mM Cys. (mL) | Sterile di water (mL) | 10× Concentration (g/L) |
|---|---|---|---|
| Cysteine (0.33 mM = 40 mg/L) | 4 | 36 | 0.4 |

3. Make 10× Tyrosine solutions at 50 mg/L.

| Test component | Tyrosine (g) | Sterile di water (mL) | 10× Concentration (g/L) |
|---|---|---|---|
| Tyrosine (50 mg/L) | 0.02 | 40 | 1 |

4. Make 10× Ascorbic acid solutions at 2.5 g/L and 10 g/L.

| Test component | Ascorbic acid (g) | Sterile di water (mL) | 10× Concentration (g/L) |
|---|---|---|---|
| Ascorbic acid (2.5 g/L) | 1 | 40 | 25 |
| Ascorbic acid (10 g/L) | 4 | 40 | 100 |

5. Make 10× Butyric acid solutions at 30 mM.

| Test component | Butyric acid (mL) | Sterile di water (mL) | 10× Concentration (mL/l) |
|---|---|---|---|
| Butyric acid (30 mM = 2.75 mL/L) | 1.1 | 38.9 | 27.5 |
| Butyric acid (60 mM = 5.5 mL/L) | 2.2 | 37.8 | 55 |

Methods

I. Medium Preparations:
1. Prepare 1000 mL SYS medium in 2 L beaker.
2. Transfer SYS to media bottles and degas for over 30 minutes with 10% $H_2$+10% $CO_2$+80% $N_2$.
3. Before transferring the medium, fill gas (10% $H_2$+10% $CO_2$+80% $N_2$) from the fill port of the Flexboy bag into the bag to remove oxygen, then empty the gas from the bag. Connect the filling system manifold with the bags.
4. For seed medium in 50 mL Flexboy bags, pump 30 mL medium into the bag from the fill port with a flow speed at 100 mL/minute.
5. For fermentation medium in 250 mL Flexboy bags:
   i) Put the bag on a balance before filling with the medium and adjust to "0".
   ii) Pump the medium into the bag from the fill port with a flow speed at 100 mL/min until the balance show 50 g, stop the pumping.
6. Move the bag for seed-1 to 37° C. $CO_2$ incubator to warm overnight. Keep bag for seed-2 and fermentation at 4° C. until use.
7. Move the bags to 37° C. $CO_2$ incubator to warm up overnight before use.
8. For different antibiotics:
   i) Prepare 40 mL solutions of different antibiotics with the concentrations at 10× (see above table).
   ii) Prepare 40 mL solutions of FE-EDTA with the concentrations at 1000 mg/L (40 mg compound+40 mL di water (pH)).
   iii) Filter the solution using the Millipore 50 mL Disposable Vacuum Filtration System with 0.22 µm Millipore Express Plus Membrane.
   iv) Before transfer of seed-2 to fermentation bags add the compound solutions at the concentrations listed in the following tables.

| Medium # | Test compound | 10× Solution (mL) | Sterile di water (mL) | Total (mL) |
|---|---|---|---|---|
| 0 | Control (without antibiotics) | 0 | 5 | 5 |
| 1 | Arginine (50 mM = 10.5 g/L) | 5 | 0 | 5 |
| 2 | Cysteine (0.33 mM = 40 mg/L) | 5 | 0 | 5 |
| 3 | Cysteine (3.3 mM = 400 mg/L) | 5 | 0 | 5 |
| 4 | Cysteine (33 mM = 4 g/L) | 5 | 0 | 5 |
| 5 | Tyrosine (50 mg/L) | 5 | 0 | 5 |
| 6 | Ascorbic acid (2.5 g/L) | 5 | 0 | 5 |
| 7 | Ascorbic acid (10 g/L) | 5 | 0 | 5 |
| 8 | Butyric acid (30 mM = 2.75 mL/l) | 5 | 0 | 5 |
| 9 | Butyric acid (60 mM = 5.5 mL/l) | 5 | 0 | 5 |

II. Fermentation Process:
1. First stage seed culture: 1 mL WCB, containing 50% glycerol, was transferred into a 50 mL Flexboy bag containing 30 mL SYS medium and incubated at 37±1° C. for 24 hours.
2. Second stage seed culture: 1.5 mL of first stage seed culture at inoculums of 5% were transferred into the 50 mL Flexboy bag containing 30 mL SYS medium and incubated at 37±1° C. for 22 hours.
3. Fermentation: 2.5 mL of second stage seed culture was inoculated at 5% for each 250 mL Flexboy bag containing 50 mL of SYS medium and incubated at 37° C.±1° C. for 24 hrs.
4. Take samples at 12 hours and 24 hours. Cell growth was measure at 600 nm. The blank of fermentation media was used as zero for the spectrophotometer. The cell concentration was diluted 10×.
5. The toxin production is measured by capture ELISA.

III. Capture ELISAs:
1. Toxin A standard Lot# CD-2062 (1072506A)
2. Goat anti-Toxin A, Lot# CD-2017
3. Mouse MAb to *C. difficile* Toxin A (PCG4)
4. Toxin B standard Lot#QC06329
5. Goat anti-Toxin B, Lot# C0210091
6. Mouse anti Toxin B Lot#030904

Results

1. The following table shows the amount of seed growth ($OD_{600\ nm}$) as measured by DU700.

| Seed-1 | Seed-2 |
|---|---|
| 2.65 | 2.53 |

2. The following table shows the amount of cell growth ($OD_{600\ nm}$) in cultures with the indicated compound.

| Test | 12 hours | 24 hours |
|---|---|---|
| Control | 2.61 | 2.61 |
| #1 Arginine (50 mM = 10.5 g/L) | 2.89 | 2.55 |
| #2 Cysteine (0.33 mM = 40 mg/L) | 2.43 | 2.36 |
| #3 Cysteine (3.3 mM = 400 mg/L) | 2.38 | 2.59 |
| #4 Cysteine (33 mM = 4 g/L) | 1.67 | 1.74 |
| #5 Tyrosine (50 mg/L) | 2.41 | 2.34 |
| #6 Ascorbic acid (2.5 g/L) | 2.49 | 2.19 |
| #7 Ascorbic acid (10 g/L) | 2.16 | 1.98 |
| #8 Butyric acid (30 mM = 2.75 mL/l) | 2.37 | 2.00 |
| #9 Butyric acid (60 mM = 5.5 mL/l) | 1.38 | 1.98 |

Figure 4A:
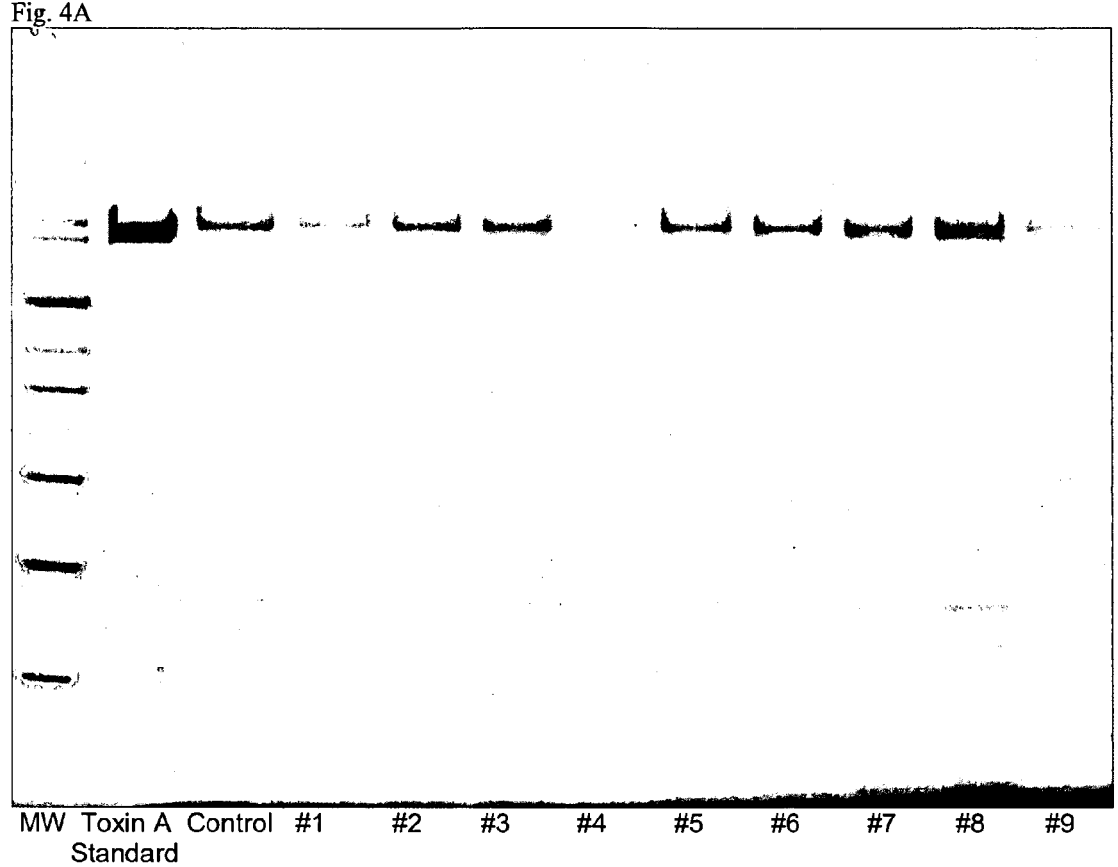
FIG. 4A is an SDS PAGE gel showing the amount of Toxin A produced in cells cultured with the indicated compounds at 12 hours. The lanes were loaded with samples from cultures including the following compounds: Control; #1 Arginine (50 mM); #2 Cysteine (0.33 mM); #3 Cysteine (3.3 mM); #4 Cysteine (33 mM); #5 Tyrosine (50 mg/L); #6 Ascorbic acid (2.5 g/L); #7 Ascorbic acid (10 g/L); #8 Butyric acid (30 mM); #9 Butyric acid (60 mM).
Figure 4B:
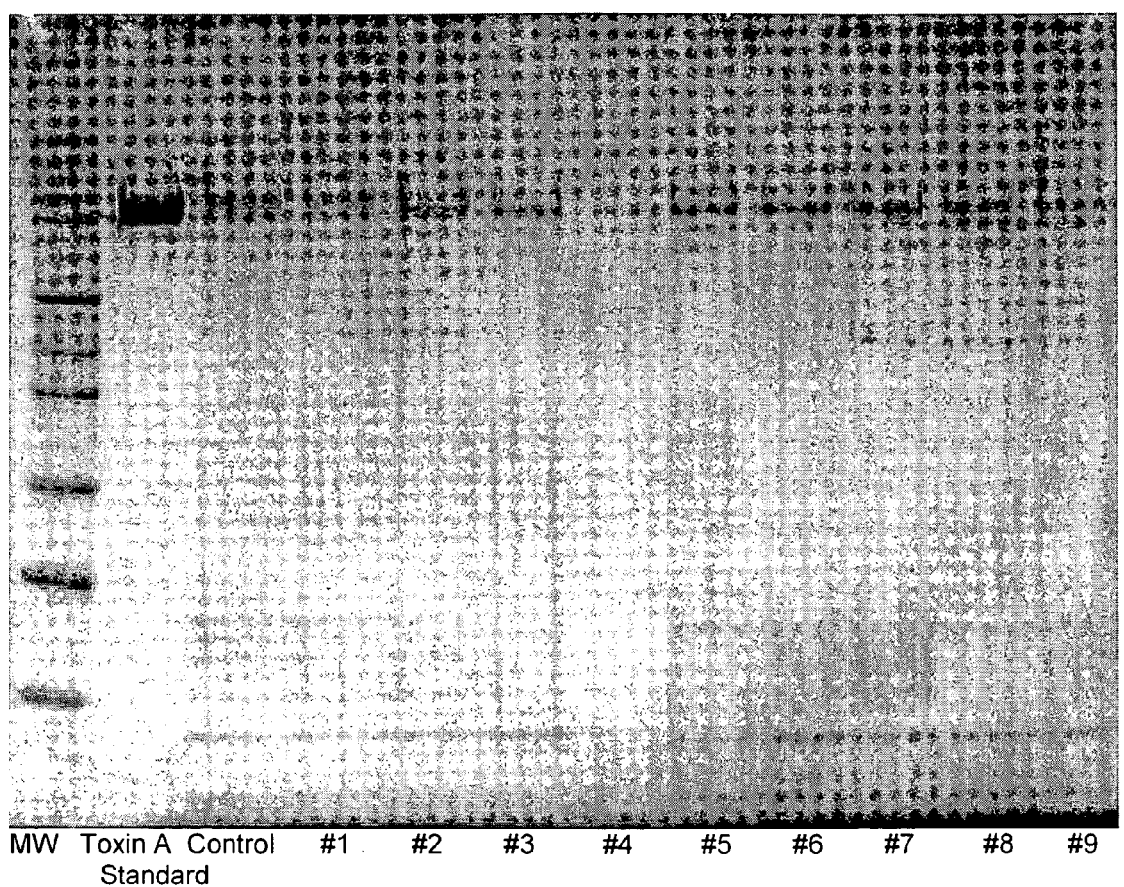
FIG. 4B is an SDS PAGE gel showing the amount of Toxin A produced in cells cultured with the indicated compounds at 24 hours. The lanes were loaded with samples from cultures including the following compounds: #1 Arginine (50 mM); #2 Cysteine (0.33 mM); #3 Cysteine (3.3 mM); #4 Cysteine (33 mM); #5 Tyrosine (50 mg/L); #6 Ascorbic acid (2.5 g/L); #7 Ascorbic acid (10 g/L); #8 Butyric acid (30 mM); #9 Butyric acid (60 mM).
Figure 5A:
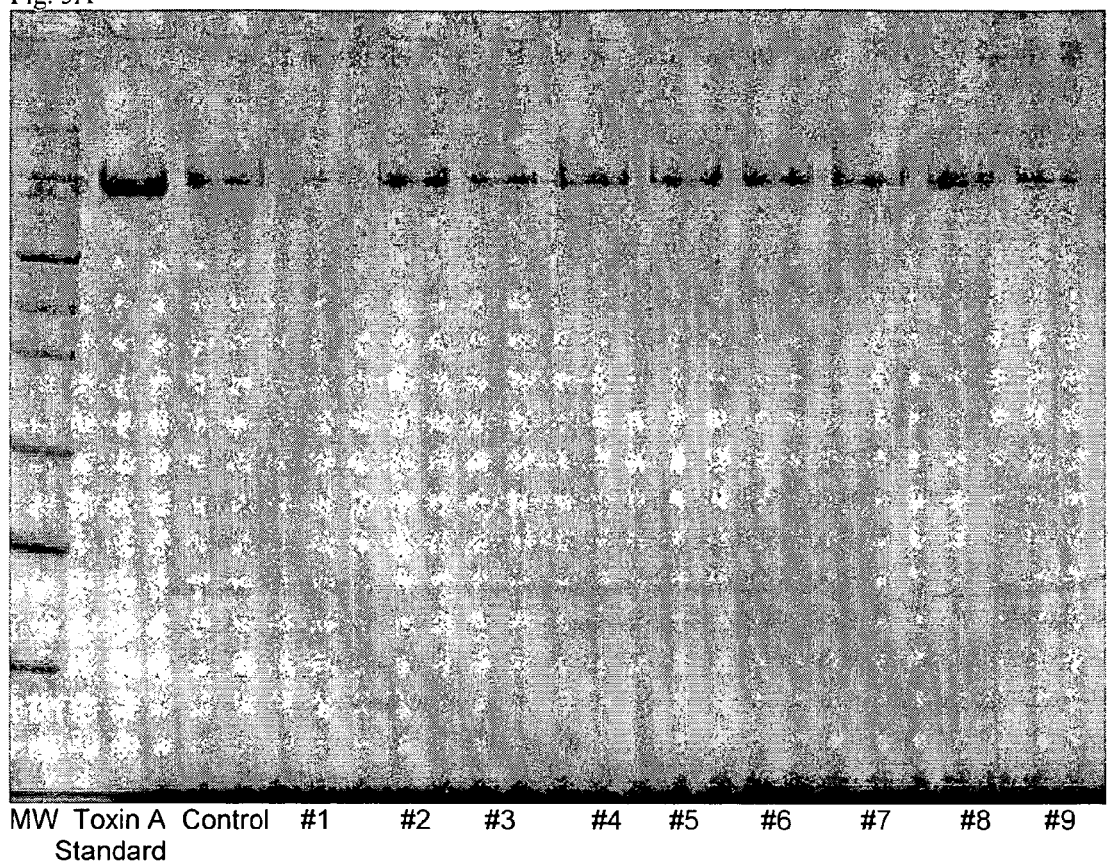
FIG. 5A is an SDS PAGE gel showing the amount of Toxin A produced in cells cultured with the indicated compounds at 12 hours. The lanes were loaded with samples from cultures including the following compounds: #1 D(−)Fructose (6 g/L); #2-D(+)Galactose (6 g/L); #3 Mannose (6 g/L); #4 Maltose Monohydrate (6 g/L); #5 Sucrose (6 g/L); #6α-Lactose (6 g/L); #7 D(+)Xylose (6 g/L); #8 D-Sorbitol (6 g/L); #9 myo-Inositol (6 g/L).
Figure 5B:
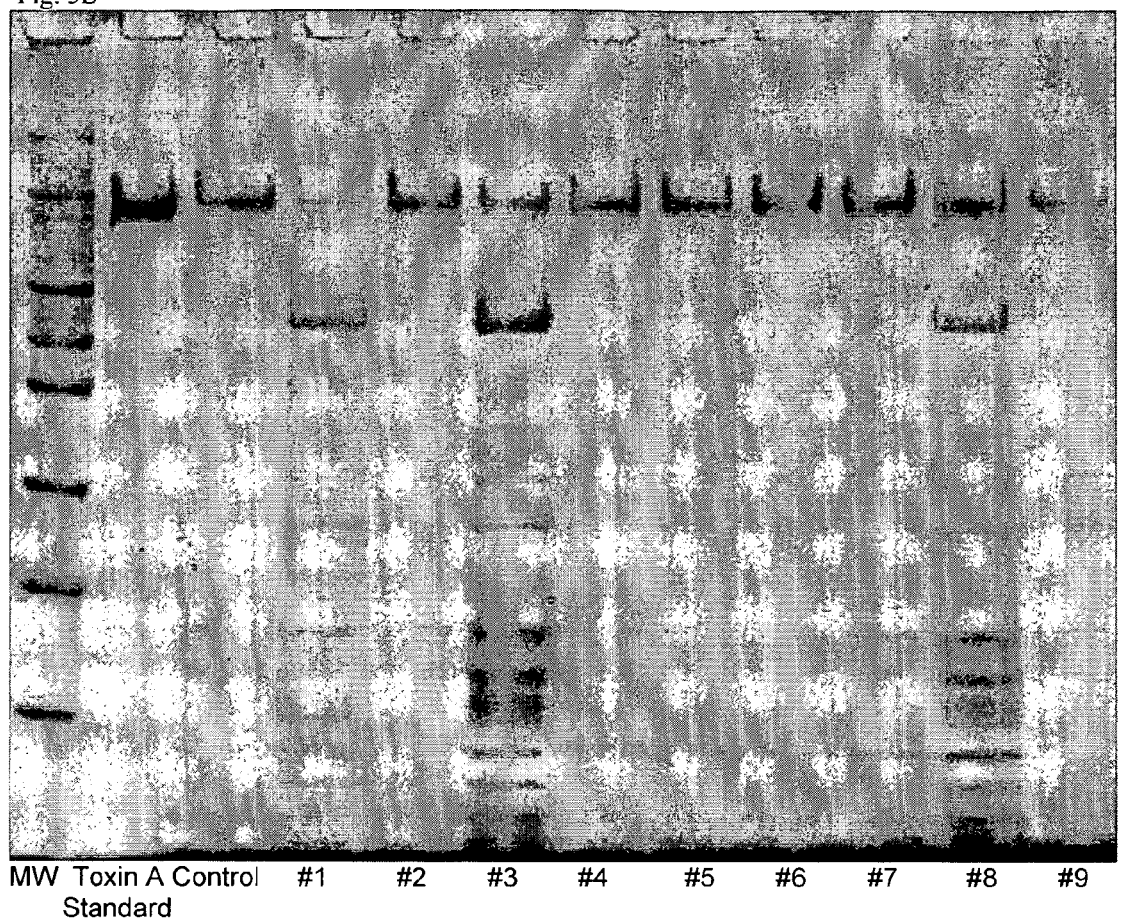
FIG. 5B is an SDS PAGE gel showing the amount of Toxin A produced in cells cultured with the indicated compounds at 24 hours. The lanes were loaded with samples from cultures including the following compounds: #1-D(−)Fructose (6 g/L); #2 D(+)Galactose (6 g/L); #3 Mannose (6 g/L); #4 Maltose Monohydrate (6 g/L); #5 Sucrose (6 g/L); #6α-Lactose (6 g/L); #7 D(+)Xylose (6 g/L); #8 D-Sorbitol (6 g/L); #9 myo-Inositol (6 g/L).

3. The following table shows the amount of Toxin A produced (ng/mL) in cultures with the indicated compound (FIGS. 4A and 4B).

| Test | 12 hours | 24 hours |
|---|---|---|
| Control | 10822 | 11515 |
| #1 Arginine (50 mM = 10.5 g/L) | 6007 | 6616 |
| #2 Cysteine (0.33 mM = 40 mg/L) | 9691 | 10365 |
| #3 Cysteine (3.3 mM = 400 mg/L) | 9828 | 10741 |
| #4 Cysteine (33 mM = 4 g/L) | 897 | 853 |
| #5 Tyrosine (50 mg/L) | 11394 | 11624 |
| #6 Ascorbic acid (2.5 g/L) | 10789 | 12050 |
| #7 Ascorbic acid (10 g/L) | 9957 | 11708 |
| #8 Butyric acid (30 mM = 2.75 mL/l) | 12315 | 12674 |
| #9 Butyric acid (60 mM = 5.5 mL/l) | 5335 | 10681 |

4. The following table shows the amount of Toxin B produced (ng/mL) in cultures with the indicated compound.

| Test | 12 hours | 24 hours |
|---|---|---|
| Control | 3825 | 3992 |
| #1 Arginine (50 mM = 10.5 g/L) | 2300 | 2626 |
| #2 Cysteine (0.33 mM = 40 mg/L) | 3446 | 3581 |
| #3 Cysteine (3.3 mM = 400 mg/L) | 3017 | 3185 |
| #4 Cysteine (33 mM = 4 g/L) | 339 | 322 |
| #5 Tyrosine (50 mg/L) | 3752 | 4462 |
| #6 Ascorbic acid (2.5 g/L) | 4026 | 4967 |
| #7 Ascorbic acid (10 g/L) | 4534 | 5955 |
| #8 Butyric acid (30 mM = 2.75 mL/l) | 5110 | 6425 |
| #9 Butyric acid (60 mM = 5.5 mL/l) | 3063 | 7529 |

5. The following table indicates cell morphological characteristics in cultures with the indicated compound.

| Test | 12 hours/24 hours |
|---|---|
| Control | Normal |
| #1 Arginine (50 mM = 10.5 g/L) | Normal |
| #2 Cysteine (0.33 mM = 40 mg/L) | Normal |
| #3 Cysteine (3.3 mM = 400 mg/L) | Normal |
| #4 Cysteine (33 mM = 4 g/L) | Cells show gray color |
| #5 Tyrosine (50 mg/L) | Normal |
| #6 Ascorbic acid (2.5 g/L) | Normal |
| #7 Ascorbic acid (10 g/L) | Normal |
| #8 Butyric acid (30 mM = 2.75 mL/l) | Normal |
| #9 Butyric acid (60 mM = 5.5 mL/l) | Normal |

6. The following table shows the amount of spore formation in 24 hour fermentation in cultures with the indicated compound. Broth was examined by microscope.

| Test | Spore formation |
|---|---|
| Control | No spore found |
| #1 Arginine (50 mM = 10.5 g/L) | Very a few spores found |
| #2 Cysteine (0.33 mM = 40 mg/L) | Very a few spores found |
| #3 Cysteine (3.3 mM = 400 mg/L) | No spore found |
| #4 Cysteine (33 mM = 4 g/L) | No spore found |
| #5 Tyrosine (50 mg/L) | No spore found |
| #6 Ascorbic acid (2.5 g/L) | No spore found |
| #7 Ascorbic acid (10 g/L) | No spore found |
| #8 Butyric acid (30 mM = 2.75 mL/l) | No spore found |
| #9 Butyric acid (60 mM = 5.5 mL/l) | No spore found |

Conclusions

Ascorbic acid, when added to SYS medium at 10 g/L, caused increases in Toxin B of 19% after 12 hours and 49% after 24 hours of incubation in fermentation broth.

Butyric Acid, when added to SYS medium at 30 mM, caused increases in Toxin A of 14% and Toxin B of 34% after 12 hours of incubation in fermentation broth. It caused increases in Toxin A of 16% and Toxin B of 61% after 24 hours of incubation in fermentation broth. Butyric Acid, when added to SYS medium at 60 mM, caused increases in Toxin B of 89% after 24 hours of incubation in fermentation broth.

Example 5

This Example includes data on the amount of toxin produced when *Clostridium difficile* is cultured in SYS basal media in the absence and presence of various concentrations of carbohydrates.

The following table summarizes the data regarding toxin increases (%) following the addition of increasing concentrations of D-sorbitol.

| D-Sorbitol Concentration | Toxin A | | Toxin B | |
|---|---|---|---|---|
| | 12 hours | 24 hours | 12 hours | 24 hours |
| 6 g/L | 25.55 | 53.98 | 45.99 | 112.30 |
| 8 g/L | 25.09 | 74.99 | 43.39 | 148.98 |
| 10 g/L | 45.47 | 140.89 | 51.76 | 216.31 |
| 12 g/L | 46.80 | 150.04 | 59.21 | 295.51 |
| 14 g/L | 23.50 | 127.69 | 27.77 | 254.23 |
| 16 g/L | 14.91 | 117.43 | 21.49 | 244.44 |
| 18 g/L | 34.90 | 136.02 | 30.00 | 236.74 |
| 20 g/L | 8.57 | 118.43 | 9.90 | 212.09 |

Materials

The following are the Example 5 test compounds, along with the compound formula and source.

D(−)Fructose: (contained <0.05% glucose) $C_6H_{12}O_6$, FW 180.2, Sigma F0127 Lot#60K0013

D(+)Galactose: $C_6H_{12}O_6$, FW 180.2, Sigma G0625, Lot#102K0169 soluble in water (1 g/1.7 mL)

D(+)Mannose: $C_6H_{12}O_6$, FW 180.16, Sigma M6020 Lot# soluble in water (50 mg/mL)

D(+)Maltose Monohydrate: (contained <0.3% glucose), $C_{12}H_{22}O_{11}\cdot H_2O$, FW 360.3, Sigma M9171 Lot#80K10101 soluble in water Sucrose: $C_{12}H_{22}O_{11}$, FW 342.3, Sigma, 53929, Lot#127K0093 soluble in water α-Lactose: $C_{12}H_{22}O_{11}\cdot H_2O$, FW 360.3, Sigma L2643, Lot# soluble in water (0.2 g/mL)

D(+)Xylose: $C_5H_{10}O_5$, FW 150.132, Sigma X3877 Lot# soluble in water (1 g/0.8 mL)

D-Sorbitol: $C_6H_{14}O_6$, FW 182.2, Sigma 53889, Lot#042K01355 soluble in water.

myo-Inositol: $C_6H_{12}O_6$, FW 180.16, Sigma 17508, Lot# soluble in water (50 mg/mL)

10× solutions of the above carbohydrates were produced.

Methods

I. Medium Preparations:
 1. Prepare 1000 mL SYS medium in 2 L beaker.
 2. Transfer SYS to media bottles and degas for over 30 minutes with 10% $H_2$+10% $CO_2$+80% $N_2$.
 3. Before transferring the medium, fill gas (10% $H_2$+10% $CO_2$+80% $N_2$) from the fill port of the Flexboy bag into the bag to remove oxygen, then empty the gas from the bag. Connect the filling system manifold with the bags.
 4. For seed medium in 50 mL Flexboy bags, pump 30 mL medium into the bag from the fill port with a flow speed at 100 mL/minute.
 5. For fermentation medium in 250 mL Flexboy bags:
  i) Put the bag on a balance before filling with the medium and adjust to "0."
  ii) Pump the medium into the bag from the fill port with a flow speed at 100 mL/min until the balance show 50 g, stop the pumping.
 6. Move the bag for seed-1 to 37° C. $CO_2$ incubator to warm overnight. Keep bag for seed-2 and fermentation at 4° C. until use.
 7. Move the bags to 37° C. $CO_2$ incubator to warm up overnight before use.
 8. For different compounds test:
  i) Prepare the solutions with different chemicals (see above table)
  ii) Filter the solution using Millipore 50 mL Disposable Vacuum Filtration System with 0.22 μm Millipore Express Plus Membrane.
  iii) Before transfer of seed-2 to fermentation bags, add the compound solutions as follows:

| Medium # | Test compound | 10× Solution (mL) | Sterile di water (mL) | Total (mL) |
|---|---|---|---|---|
| 0 | Control (without carbohydrate additive) | 0 | 5 | 5 |
| 1 | D(−)Fructose (6 g/L) | 5 | 0 | 5 |
| 2 | D(+)Galactose (6 g/L) | 5 | 0 | 5 |
| 3 | D(+)Mannose (6 g/L) | 5 | 0 | 5 |
| 4 | D(+)Maltose Monohydrate (6 g/L) | 5 | 0 | 5 |
| 5 | Sucrose (6 g/L) | 5 | 0 | 5 |
| 6 | α-Lactose (6 g/L) | 5 | 0 | 5 |
| 7 | D(+)Xylose (6 g/L) | 5 | 0 | 5 |
| 8 | D-Sorbitol (6 g/L) | 5 | 0 | 5 |
| 9 | myo-Inositol (6 g/L) | 5 | 0 | 5 |

II. Fermentation Process:
1. First stage seed culture: 1 mL WCB, containing 50% glycerol, was transferred into a 50 mL Flexboy bag containing 30 mL SYS medium and incubated at 37±1° C. for 24 hours.
2. Second stage seed culture: 1.5 mL of first stage seed culture at inoculums of 5% were transferred into the 50 mL Flexboy bag containing 30 mL SYS medium and incubated at 37±1° C. for 22 hours.
3. Fermentation: 2.5 mL of second stage seed culture was inoculated at 5% for each 250 mL Flexboy bag containing 50 mL of SYS medium and incubated at 37° C.±1° C. for 24 hours
4. Take samples at 12 hours and 24 hours. Cell growth was measure at 600 nm. The blank of fermentation media was used as zero for the spectrophotometer. The cell concentration was diluted 10×.
5. The toxin production is measured by capture ELISA.

III. Capture ELISAs:
1. Toxin A standard Lot# CD-2062 (1072506A)
2. Goat anti-Toxin A, Lot# CD-2017
3. Mouse MAb to *C. difficile* Toxin A (PCG4)
4. Toxin B standard Lot#QC06329
5. Goat anti-Toxin B, Lot# C0210091
6. Mouse anti Toxin B Lot#030904

Results

1. The following table shows the amount of seed growth ($OD_{600\ nm}$) as measured by DU700.

| Seed-1 | Seed-2 |
|---|---|
| 2.57 | 2.561 |

2. The following table shows the amount of cell growth ($OD_{600\ nm}$) in cultures with the indicated compound.

| Test | 12 hours | 24 hours |
|---|---|---|
| Control (without carbohydrate additive) | 2.78 | 2.57 |
| #1 D(−)Fructose (6 g/L) | 3.42 | 2.21 |
| #2 D(+)Galactose (6 g/L) | 2.92 | 2.51 |
| #3 D(+)Mannose (6 g/L) | 5.14 | 2.84 |
| #4 D(+)Maltose Monohydrate (6 g/L) | 2.91 | 2.80 |
| #5 Sucrose (6 g/L) | 2.74 | 2.62 |
| #6 α-Lactose (6 g/L) | 2.57 | 2.36 |
| #7 D(+)Xylose (6 g/L) | 3.34 | 3.53 |
| #8 D-Sorbitol (6 g/L) | 4.00 | 3.35 |
| #9 myo-Inositol (6 g/L) | 2.61 | 2.53 |

3. The following table shows the amount of Toxin A produced (ng/mL) in cultures with the indicated compound (FIGS. 5A and 5B).

| Test | 12 hours | 24 hours |
|---|---|---|
| Control | 10108 | 10508 |
| #1 D(−)Fructose (6 g/L) | 1031 | 2146 |
| #2 D(+)Galactose (6 g/L) | 8596 | 9154 |
| #3 D(+)Mannose (6 g/L) | 3568 | 5288 |
| #4 D(+)Maltose Monohydrate (6 g/L) | 8741 | 8764 |
| #5 Sucrose (6 g/L) | 11042 | 10881 |
| #6 α-Lactose (6 g/L) | 9258 | 10167 |
| #7 D(+)Xylose (6 g/L) | 10135 | 11565 |
| #8 D-Sorbitol (6 g/L) | 15080 | 19575 |
| #9 myo-Inositol (6 g/L) | 8189 | 8743 |

4. The following table shows the amount of Toxin B produced (ng/mL) in cultures with the indicated compound.

| Test | 12 hours | 24 hours |
|---|---|---|
| Control | 3756 | 3832 |
| #1 D(−)Fructose (6 g/L) | 319 | 755 |
| #2 D(+)Galactose (6 g/L) | 3071 | 3379 |
| #3 D(+)Mannose (6 g/L) | 1518 | 2123 |
| #4 D(+)Maltose Monohydrate (6 g/L) | 3079 | 3022 |
| #5 Sucrose (6 g/L) | 3902 | 4235 |
| #6 α-Lactose (6 g/L) | 3126 | 3655 |
| #7 D(+)Xylose (6 g/L) | 4075 | 5588 |
| #8 D-Sorbitol (6 g/L) | 6311 | 9696 |
| #9 myo-Inositol (6 g/L) | 2743 | 3196 |

5. The following table indicates cell morphological characteristics in cultures with the indicated compound.

| Test | 12 hours/24 hours |
|---|---|
| Control | Normal |
| #1 D(−)Fructose (6 g/L) | Cell lyse at 24 hours |
| #2 D(+)Galactose (6 g/L) | Normal |
| #3 D(+)Mannose (6 g/L) | Cell lyse at 24 hours |
| #4 D(+)Maltose Monohydrate (6 g/L) | Normal |
| #5 Sucrose (6 g/L) | Normal |
| #6 α -Lactose (6 g/L) | Normal |
| #7 D(+)Xylose (6 g/L) | Normal |
| #8 D-Sorbitol (6 g/L) | Cell lyse at 24 hours |
| #9 myo-Inositol (6 g/L) | Normal |

6. The following table shows the amount of spore formation in 24 h fermentation in cultures with the indicated compound. Broth was examined by microscope.

| Test | Spore formation |
|---|---|
| Control | No spore found |
| #1 D(−)Fructose (6 g/L) | No spore found |
| #2 D(+)Galactose (6 g/L) | No spore found |
| #3 D(+)Mannose (6 g/L) | No spore found |
| #4 D(+)Maltose Monohydrate (6 g/L) | No spore found |
| #5 Sucrose (6 g/L) | No spore found |
| #6 α -Lactose (6 g/L) | No spore found |
| #7 D(+)Xylose (6 g/L) | No spore found |
| #8 D-Sorbitol (6 g/L) | No spore found |
| #9 myo-Inositol (6 g/L) | No spore found |

Conclusions

D(+)Xylose, when added to SYS medium at 6 g/L, slightly increased cell growth and Toxin A production. D(+)Xylose increased Toxin B production 9% after 12 hours of incubation in fermentation broth and 46% after 24 hours of incubation in fermentation broth.

D-Sorbitol, when added to SYS medium at 6 g/L, markedly increased cell growth and toxins production. Cell growth was increased 44% after 12 hours of incubation in fermentation broth. Toxin A production was increased 49% after 12 hours of incubation in fermentation broth and 86% after 24 hours of incubation in fermentation broth. Toxin B production was increased 68% after 12 hours of incubation in fermentation broth and 153% after 24 hours of incubation in fermentation broth.

Example 6

This example includes data on the amount of toxin produced when *Clostridium difficile* is cultured in SYS basal media supplemented with D-Sorbitol (12 g/L) under pH controlled conditions.

Materials

The following materials and equipment were used in this example.

A Biostat B Plus Fermentation System (Sartorius) was used for the first stage seed culture and second stage seed culture, using 2×2 L fermenters (Sartorius), one for each seed culture seed. A Biostat Q Plus Fermentation System (Sartorius) was used for the third stage seed culture using 4×1 L fermenters (Sartorius). A peristalitic pump (Masterflex) was used to transfer media for both systems. Media composition for the seed stages were as follows:

| SYS media | | |
|---|---|---|
| Component | Manufacturer/Lot # | Formulation (g/L) |
| $KH_2PO_4$ | J T Baker/E29H22 | 0.9 |
| $Na_2PO_4$ | J T Baker/A12145 | 5 |
| $NaHCO_3$ | J T Baker/A13668 | 5 |
| Soy Peptone A3 SC | Organotechnie/19685 | 30 |
| Yeast Extract | BD Bacto/7109497 | 20 |

Media composition for the production stage was as follows:

| SYS media + Sorbitol | | |
|---|---|---|
| Component | Manufacturer/Lot # | Formulation (g/L) |
| $KH_2PO_4$ | J T Baker/E29H22 | 0.9 |
| $Na_2PO_4$ | J T Baker/A12145 | 5 |
| $NaHCO_3$ | J T Baker/A13668 | 5 |
| Soy Peptone A3 SC | Organotechnie/19685 | 30 |
| Yeast Extract | BD Bacto/7109497 | 20 |
| D-Sorbitol(70%)* | Spectrum/WJ1030 | 17.1 ml |

*17.1 ml of D-Sorbitol (70%) represents 12 g/L

The SYS media and SYS media+Sorbitol were each prepared using reverse osmosis deionized water (RODI-water). Additional materials included:

| | Manufacturer/Lot # | Part # | Qty. Added |
|---|---|---|---|
| Working Cell Bank vial, WCB-A, 4.5 ml | In-house | n/a | 0.5 (2 ml) |
| Anaerobic Gas mix(80% N2/10% CO2/10% H2) | | RM-0024 | 20 |
| 5N Sodium Hydroxide | J T Baker/E17507 | 5671-06 | 1 L |
| 1N Hydrochloric Acid | J T Baker/B08510 | 5618-02 | 200 ml |

Methods

The following methods were used to test the production of Toxin A and B when cultured under pH controlled conditions.

I. Seed Bioreactor 1
1. A 2 L vessel was prepared with a ring sparger and a pitched blade impeller on the bottom of the shaft set at a 45° angle.
2. A pH probe was calibrated according to Sartorius procedures and installed in the bioreactor.
3. The bioreactor was then autoclaved on a dry cycle for 30 min with 10 min pre and post-vacuum cycles.
4. After sterilization, the sterile vessel was connected to the Biostat B Plus System.
5. SYS medium was prepared as described above
6. 1600 mL of medium were aseptically transferred to the sterile bioreactor.
7. Vessel temperature and agitation were set to 37° C. and 100 rpm, respectively.
8. Prior to inoculation, the bioreactor was de-gassed by sparging with anaerobic gas mix at 300 mL/min for 15 minutes.
9. 4 mL of WCB-A was aseptically transferred to the bioreactor to initiate the culture.
10. During the culture, the bioreactor was sparged with anaerobic gas mix at 100 mL/min and incubated for 18 h.
11. At end of 18 hr, a 5 ml sample was taken for OD measurement.

II. Seed Bioreactor 2
1. A 2 L vessel was prepared with a ring sparger and a pitched blade impeller on the bottom of the shaft set at a 45° angle.
2. A pH probe was calibrated according to Sartorius procedures and installed in the bioreactor.
3. The bioreactor was then autoclaved on a dry cycle for 30 min with 10 min pre and post-vacuum cycles.
4. After sterilization, the sterile vessel was connected to the Biostat B Plus System.
5. SYS medium was prepared as described above
6. 1800 mL of medium were aseptically transferred to the sterile bioreactor.
7. Vessel temperature and agitation were set to 37° C. and 100 rpm, respectively.
8. Prior to inoculation, medium in vessel was sparged with anaerobic gas mix at 300 mL/min for 15 minutes.
9. 100 mL of the 1st stage culture was aseptically transferred the 2nd stage.
10. During the culture, the bioreactor was sparged with anaerobic gas mix at 100 mL/min and incubated for 10 h.
11. At end of 10 hr, a 5 ml sample was taken for OD measurement.

III. Production Bioreactor
1. 4×1 L vessels were prepared each with a ring sparger and a pitched blade impeller on the bottom of the shaft set at ~45° angle.
2. A pH probe for each bioreactor was calibrated according to Sartorius procedures and installed in each bioreactor.
3. All bioreactors were then autoclaved on a dry cycle for 30 min with 10 min pre and post-vacuum cycles.
4. After sterilization, the bioreactors were connected to the Biostat Q Plus System.
5. SYS medium+Sorbitol was prepared as described above
6. 900 mL of medium was aseptically transferred to each bioreactor.
7. Acid and base bottles were autoclaved, aseptically filled with sterile filtered 1N HCl and 5N NaOH, respectively, and attached to the bioreactors.
8. Agitiaton was set to 100 rpm for all bioreactors.
9. The desired temperature and pH control set points were implemented (see Table 5).

10. Prior to inoculation, bioreactors were de-gassed by sparging with appropriate gas (see Table 5) for 30 minutes at 300 mL/min.
11. Each vessel was inoculated with ~100 mL of culture from Seed Bioreactor 2.
12. $3^{rd}$ stage cultures were incubated at 37° C. with no additional sparging for 18 hours.
13. Samples (~5 mL) were taken at appropriate times for OD and toxin measurements, typically between 14.5 to 18 hrs post-inoculation.
14. For ELISA, 2×1 mL of sample were spun in 1.8 mL microcentrifuge tubes at 10,000 g for 1 min, then decanted and 0.2 μm filtered. The samples were stored at 2-8° C. until tested.

TABLE 5

| Vessel No. | Volume (ml) | Inoc (ml) | Temp ° C. | Stirrer (rpm) | pH Control* | NaHCO$_3$ (g/L) | Degas Gas | Sparge Gas | Culture Stage |
|---|---|---|---|---|---|---|---|---|---|
| B1 | 800 | 2 | 37 | 100 | None | 5 | Gas mix | Gas mix | $1^{st}$ stage |
| B2 | 900 | 100 | 37 | 100 | None | 5 | Gas mix | Gas mix | $2^{nd}$ stage |
| QA1 | 900 | 100 | 37 | 100 | 6.5 | 5 | Gas mix | None | $3^{rd}$ stage |
| QA2 | 900 | 100 | 37 | 100 | 7.2 | 5 | Gas mix | None | $3^{rd}$ stage |
| QA3 | 900 | 100 | 37 | 100 | 8.0 | 5 | Gas mix | None | $3^{rd}$ stage |
| QB3 | 900 | 100 | 37 | 100 | None | 5 | Gas mix | None | $3^{rd}$ stage |

*pH control using 1N HCl, 5N NaOH

Results

The following table shows total cell growth (OD 600 nm) and the amount of Toxin A produced (ng/ml) and Toxin B produced (ng/ml) in the cultures subject to the indicated pH control (FIGS. 6A, 6B).

| Sample | OD@600 nm | Toxin A (ng/ml) | Toxin B (ng/ml) |
|---|---|---|---|
| 1 stage @18 hrs | 1.96 | N/A | N/A |
| $2^{nd}$ stage @10 hrs | 2.71 | N/A | N/A |
| Control @14.5 hrs | 4.02 | 27006 | 11296 |
| Control @16.25 hrs | 4.37 | 29141 | 11916 |
| Control @18 hrs | 4.32 | 32247 | 14522 |
| pH 6.5 @14.5 hrs | 3.08 | 32144 | 14400 |
| pH 6.5 @16.25 hrs | 3.32 | 34301 | 13731 |
| pH 6.5 @18 hrs | 3.56 | 36511 | 15578 |
| pH 7.2 @14.5 hrs | 5.17 | 16447 | 6258 |
| pH 7.2 @16.25 hrs | 5.12 | 17739 | 6609 |
| pH 7.2 @18 hrs | 5.12 | 21214 | 7368 |
| pH 8.0 @14.5 hrs | 4.56 | 1095 | 191* |
| pH 8.0 @16.25 hrs | 4.38 | 1451 | 318* |
| pH 8.0 @18 hrs | 3.61 | 1500 | 281* |

*Below LOQ at dilution tested

Conclusions

The highest yields of both Toxin A and Toxin B were produced by maintaining the pH of the culture at a low pH (i.e., 6.5). The control culture, which was subject to no pH control also showed significantly more toxin production than those cultures subjected to a controlled pH 7.2 or pH 8.0. Lacking pH control, the pH of the control culture declined naturally (typically, declining from a starting pH of approximately pH 7.3 to a final pH of approximately 6.3).

SDS-Page gels showed similar bands and intensities for the control and pH 6.5, with the only differences being in the intensity of a band in the 100 kDa range.

Example 7

This example includes data on the amount of toxin produced when *Clostridium difficile* is cultured under pH controlled conditions in SYS basal media having a reduced sodium bicarbonate concentration of 2 g/L and supplemented with D-Sorbitol (12 g/L).

The materials and methods utilized in this experiment were as set out in Example 6, except as noted below.

Materials

SYS media+Sorbitol included 2 g/L NaHCO$_3$ (reduced from 5 g/L used in Example 6)

Methods

III. Production Bioreactor 1. 5×1 L vessels ($3^{rd}$ stage vessels: QB2, QB3, QA1, QA2, QA3) were prepared in 2 sets (of 2 and 3). The desired temperature and pH control setpoints were implemented (see Table 6).
2. Prior to inoculation, bioreactors were sparged with an appropriate gas for 30 minutes at 300 mL/min (see Table 6).
3. $3^{rd}$ stage cultures were incubated at 37° C. with no gassing for 21 hours.

TABLE 6

| Vessel No. | Volume (ml) | Inoc (ml) | Temp ° C. | Stirrer (rpm) | pH Control* | NaHCO$_3$ (g/L) | Degas Gas | Sparge Gas | Culture Stage |
|---|---|---|---|---|---|---|---|---|---|
| B1 | 1600 | 4 | 37 | 100 | None | 5 | Gas mix | Gas mix | $1^{st}$ stage |
| B2 | 1800 | 200 | 37 | 100 | None | 5 | Gas mix | Gas mix | $2^{nd}$ stage |
| QA1 | 900 | 100 | 37 | 100 | 7.0 | 2 | Gas mix | None | $3^{rd}$ stage |
| QA2 | 900 | 100 | 37 | 100 | 7.5 | 2 | Gas mix | None | $3^{rd}$ stage |
| QA3 | 900 | 100 | 37 | 100 | None | 2 | Gas mix | None | $3^{rd}$ stage |
| QB2 | 900 | 100 | 37 | 100 | 6.0 | 2 | 100% CO$_2$ | None | $3^{rd}$ stage |
| QB3 | 900 | 100 | 37 | 100 | 6.5 | 2 | 100% CO$_2$ | None | $3^{rd}$ stage |

*pH control using 1N HCl, 5N NaOH

Results

1. The following table shows total cell growth (OD 600 nm) and the amount of Toxin A produced (ng/ml) and Toxin B produced (ng/ml) in the cultures subject to the indicated pH control (FIGS. 7A, 7B).

| Sample (Vessel No.) | OD@600 nm | Toxin A (ng/ml) | Toxin B (ng/ml) |
|---|---|---|---|
| 1st stage 18 h | 1.59 | N/A | N/A |
| 2nd stage 10 h | 2.64 | N/A | N/A |
| pH 6.0 15 h (QB2) | 1.55 | 10364 | 6670 |
| pH 6.5 15 h (QB3) | 2.82 | 26012 | 16119 |
| pH 7.0 15 h (QA1) | 4.73 | 24928 | 12383 |
| pH 7.5 15 h (QA2) | 4.93 | 7688 | 2292 |
| Control 15 h (QA3) | 3.25 | 30259 | 20561 |
| pH 6.0 18 h (QB2) | 1.49 | 9047 | 5785 |
| pH 6.5 18 h (QB3) | 3.21 | 33477 | 20031 |
| pH 7.0 18 h (QA1) | 5.39 | 24702 | 10588 |
| pH 7.5 18 h (QA2) | 4.55 | 7694 | 1882 |
| Control 18 h (QA3) | 3.72 | 46454 | 22015 |
| pH 6.0 21 h (QB2) | 1.75 | 13473 | 5254 |
| pH 6.5 21 h (QB3) | 3.53 | 38631 | 17972 |
| pH 7.0 21 h (QA1) | 4.83 | 29123 | 10538 |
| pH 7.5 21 h (QA2) | 4.96 | 7484 | 1816 |
| Control 21 h (QA3) | 4.01 | 41521 | 20046 |

2. Specific Toxin A productivity produced (ng/ml per OD unit) in the cultures subject to the indicated pH control is set out in FIG. 7C. Specific Toxin B productivity produced (ng/ml per OD unit) in the cultures subject to the indicated pH control is set out in FIG. 7D.

Conclusions

Lowering the sodium bicarbonate to 2 g/L in the SYS+Sorbitol medium allowed for a lower starting pH with less acid and/or $CO_2$ sparged. It is possible to achieve a pH of 6.5 without the addition of acid, by sparging with $CO_2$.

The uncontrolled pH condition in this experiment had at least equivalent total Toxin B production and slightly higher total Toxin A production than the pH 6.5 condition. Specific toxin production was similar for the uncontrolled and pH 6.5 conditions.

FIG. 7E depicts a comparison of the results from this experiment and that set out in Example 6. FIG. 7E shows total toxin concentration at 18 h for various conditions over the 2 experiments. A clear drop-off in toxin production is seen in cultures at pH 6.5 to pH 6.0 and a more gradual decline in toxin production in the higher pH conditions. The optimal pH is slightly higher than 6.5.

Example 8

This example includes data on the effect of different concentrations of sodium bicarbonate (i.e., 0 g/L, 2 g/L, and 5 g/L) and carbon dioxide sparing on the pH of SYS basal media supplemented with D-Sorbitol (12 g/L).

Materials

The following materials and equipment were used in this example.

The Biostat Q Plus Fermentation System (Sartorius) was used for the first, second, and third stage cultures, using three 1 L fermenters (Sartorius). The composition of the SYS media supplemented with D-Sorbitol (SYS media+Sorbitol) was as described in Example 6, except that no $NaHCO_3$ was added to the initial 4 L batch prepared.

Methods

The following methods were used to test changes in pH.
1. 3 pH probes were calibrated on the Biostat Q Plus system
2. 4 L of SYS media with sorbitol was made without sodium bicarbonate and 1 L was added to a 1 L fermenter.
3. 6 g of sodium bicarb was added to the remaining 3 L of media for a bicarb concentration of 2 g/L. 1 L of the media was added to a 1 L fermenter.
4. 6 g of sodium bicarb was added to the remaining 2 L of media for a bicarb concentration of 5 g/L. 1 L of the media was added to a 1 L fermenter.
5. All fermenters were mixed at 100 rpm and the pH probes were installed
6. 100% $CO_2$ was sparged at 500 ml/min and the data acquisition software was started to generate pH curves
7. After ~3.5 hours, 5 ml of 5N HCl was added to each fermenter.

Results

1. The following table shows the pH changes noted using different concentrations of sodium bicarbonate.

| Condition | Starting pH | Lowest pH with $CO_2$ sparging | pH with 5 ml 5N HCl added |
|---|---|---|---|
| 0 g/L Bicarb | 7.15 | 6.18 | 5.72 |
| 2 g/L Bicarb | 7.15 | 6.28 | 5.94 |
| 5 g/L Bicarb | 7.12 | 6.4 | 6.1 |

Conclusions

A lower final pH can be achieved in SYS medium with a lower sodium bicarbonate concentration when gassing with $CO_2$. Using 2 g/L bicarb can lower the pH by 0.12 units with $CO_2$ sparge alone compared to 5 g/L.

Example 9

This example includes data on the amount of toxin produced when *Clostridium difficile* is cultured in SYS basal media supplemented with D-Sorbitol (12 g/L) with different concentrations of sodium bicarbonate (i.e., 0 g/L, 2 g/L, and 5 g/L) and spared with carbon dioxide or an anaerobic gas mix (80% $N_2$/10% $CO_2$/10% $H_2$).

The materials and methods utilized in this experiment were as set out in Example 6, except as noted below.

Materials

The composition of the SYS media for the first stage seed cultures was as described in Example 6. For the third stage cultures, an SYS media supplemented with Sorbitol was prepared having the following composition and using RODI-water:

| SYS media + Sorbitol | | |
|---|---|---|
| Component | Manufacturer/Lot # | Formulation (g/L) |
| $KH_2PO_4$ | J T Baker/E29H22 | 0.9 |
| $Na_2PO_4$ | J T Baker/A12145 | 5 |
| $NaHCO_3$ | J T Baker/A13668 | 0 |
| Soy Peptone A3 SC | Organotechnie/19685 | 30 |
| Yeast Extract | BD Bacto Part#21270/Lot #8352570 | 20 |
| D-Sorbitol (70%) | Spectrum/WJ1030 | 17.1 ml |

Two separate batches of SYS media+Sorbitol culture media were also prepared having the same composition but with a different concentration of $NaHCO_3$ (i.e., one with $NaHCO_3$ 2 g/L and one with 5 g/L $NaHCO_3$).

Methods

III. Production Bioreactor 1. 5×1 L vessels (3$^{rd}$ stage vessels: QB2, QB3, QA1, QA2, QA3) were prepared in 2 sets (of 2 and 3). The desired temperature and pH control setpoints were implemented (see Table 7).
2. Prior to inoculation, bioreactors were sparged with an appropriate gas for 30 minutes at 300 mL/min (see Table 7).
3. 3$^{rd}$ stage cultures were incubated at 37° C. with no gassing for 21 hours.

TABLE 7

| Vessel No. | Volume (ml) | Inoc (ml) | Temp ° C. | Stirrer (rpm) | pH Control* | NaHCO$_3$ (g/L) | Degas Gas | Sparge Gas | Culture Stage |
|---|---|---|---|---|---|---|---|---|---|
| B1 | 1600 | 4 | 37 | 100 | None | 5 | Gas mix | Gas mix | 1$^{st}$ stage |
| B2 | 1800 | 200 | 37 | 100 | None | 5 | Gas mix | Gas mix | 2$^{nd}$ stage |
| QA1 | 900 | 100 | 37 | 100 | None | 0 | Gas mix | None | 3$^{rd}$ stage |
| QA2 | 900 | 100 | 37 | 100 | None | 2 | Gas mix | None | 3$^{rd}$ stage |
| QA3 | 900 | 100 | 37 | 100 | None | 5 | Gas mix | None | 3$^{rd}$ stage |
| QB2 | 900 | 100 | 37 | 100 | 6.5 | 2 | 100% CO$_2$ | None | 3$^{rd}$ stage |
| QB3 | 900 | 100 | 37 | 100 | 6.5 | 2 | Gas mix | None | 3$^{rd}$ stage |

*pH control using 1N HCl, 5N NaOH

Results

Figures 8A, 8B:
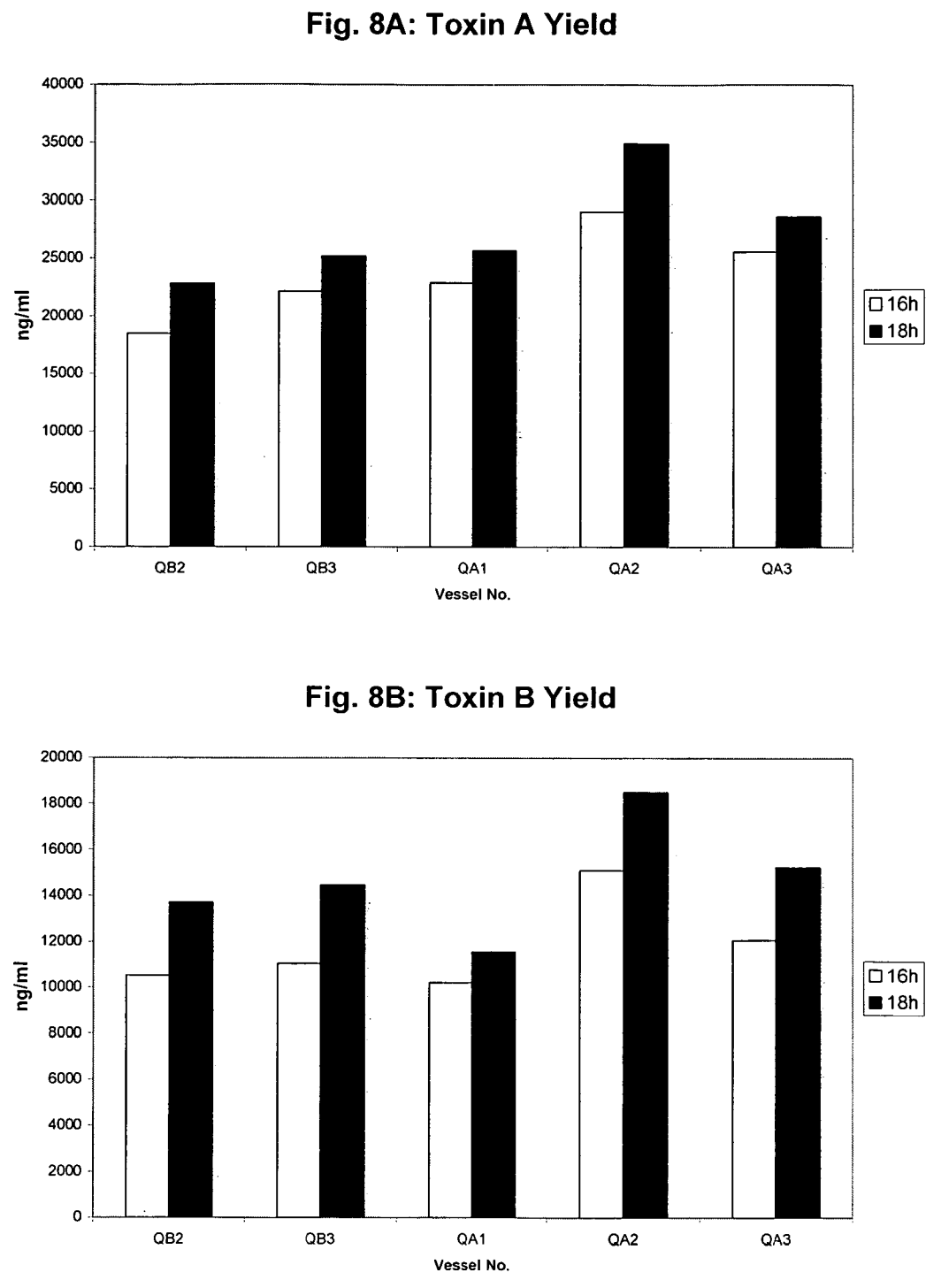

1. The following table shows total cell growth (OD 600 nm) and the amount of Toxin A produced (ng/ml) and Toxin B produced (ng/ml) in the cultures subject to the indicated pH control (FIGS. 8A, 8B).

| Sample | OD@600 nm | Toxin A (ng/ml) | Toxin B (ng/ml) |
|---|---|---|---|
| 1$^{st}$ stage 18 h | 0.76 | N/A | N/A |
| 2$^{nd}$ stage 10 h | 2.27 | N/A | N/A |
| QB2- pH 6.5 CO$_2$ 16 h | 2.82 | 18519 | 10519 |
| QB3- pH 6.5 gas mix 16 h | 2.71 | 22109 | 11051 |
| QA1- 0 g/L bicarb 16 h | 2.73 | 22898 | 10217 |
| QA2- 2 g/L bicarb 16 h | 3.22 | 29048 | 15099 |
| QA3- 5 g/L bicarb 16 h | 4.02 | 25579 | 12087 |
| QB2- pH 6.5 CO2 18 h | 2.98 | 22820 | 13695 |
| QB3- pH 6.5 gas mix 18 h | 2.97 | 25185 | 14463 |
| QA1- 0 g/L bicarb 18 h | 3.15 | 25688 | 11576 |
| QA2- 2 g/L bicarb 18 h | 3.5 | 34927 | 18500 |
| QA3- 5 g/L bicarb 18 h | 3.86 | 28656 | 15256 |

2. The 1st stage cell growth in this experiment was lower than typically seen in this experiment. There was not a significant difference in the growth or toxin production of the fermentations controlled at pH 6.5 with either CO$_2$ or anaerobic gas mix sparging. A sodium bicarbonate concentration of 2 g/L sodium bicarbonate provided a higher specific and total toxin A and B productivity compared to concentrations of 0 g/L and 5 g/L.

Conclusions

The use of CO$_2$ for degassing the media is an option when controlling pH at 6.5 because of the comparable toxin yields to the anaerobic gas mix degassed fermentation.

Example 10

This example includes data on the amount of toxin produced when *Clostridium difficile* is cultured under a range of temperatures (37-41° C. with a midpoint of 39° C.) and a range of pH (6.35 to 6.65 with a midpoint of 6.5) in SYS basal media supplemented with D-Sorbitol (12 g/L).

The materials and methods utilized in this experiment were as set out in Example 6, except as noted below.

Materials

The composition of the SYS media for the first stage seed cultures was as described in Example 6. For the third stage cultures, an SYS media supplemented with Sorbitol was prepared having the following composition and using RODI-water:

| SYS media + Sorbitol | | |
|---|---|---|
| Component | Manufacturer/Part #/Lot # | Formulation (g/L) |
| KH$_2$PO$_4$ | J T Baker/3248-07/Y48478 | 0.9 |
| Na$_2$PO$_4$ | J T Baker/3827-01/B08143 | 5 |
| NaHCO$_3$ | J T Baker/3509-05/E05589 | 2 |
| Soy Peptone A3 SC | Organotechnie/130-127-00/19685 | 30 |
| Yeast Extract | BD Bacto/212720/8352570 | 20 |
| D-Sorbitol (70%) | Spectrum/S0220/WJ1030 | 17.1 ml |

Methods

III. Production Bioreactor 1. 6×1 L vessels (3$^{rd}$ stage vessels: QB1, QB2, QB3, QA1, QA2, QA3) were prepared in 2 sets (of 2 and 3). The desired temperature and pH control setpoints were implemented (see Table 8).
2. Prior to inoculation, bioreactors were sparged with an appropriate gas for 30 minutes at 300 mL/min (see Table 8).
3. 3$^{rd}$ stage cultures were incubated at the applicable temperature with no gassing for 21 hours.

TABLE 8

| Vessel No. | Volume (ml) | Inoc (ml) | Temp ° C. | Stirrer (rpm) | pH Control | NaHCO$_3$ (g/L) | Degas Gas | Sparge Gas | Culture Gas |
|---|---|---|---|---|---|---|---|---|---|
| B1 | 1600 | 4 | 37 | 100 | None | 5 | Gas mix | Gas mix | 1$^{st}$ stage |
| B2 | 1800 | 200 | 37 | 100 | None | 5 | Gas mix | Gas mix | 2$^{nd}$ stage |
| QA1 | 900 | 100 | 39 | 100 | None | 2 | Gas mix | none | 3$^{rd}$ stage |

TABLE 8-continued

| Vessel No. | Volume (ml) | Inoc (ml) | Temp °C. | Stirrer (rpm) | pH Control | NaHCO$_3$ (g/L) | Degas Gas | Sparge Gas | Culture Gas |
|---|---|---|---|---|---|---|---|---|---|
| QA2 | 900 | 100 | 39 | 100 | 6.5 | 2 | Gas mix | none | 3$^{rd}$ stage |
| QA3 | 900 | 100 | 37 | 100 | 6.35 | 2 | Gas mix | none | 3$^{rd}$ stage |
| QB1 | 900 | 100 | 37 | 100 | 6.65 | 2 | Gas mix | none | 3$^{rd}$ stage |
| QB2 | 900 | 100 | 41 | 100 | 6.35 | 2 | Gas mix | none | 3$^{rd}$ stage |
| QB3 | 900 | 100 | 41 | 100 | 6.65 | 2 | Gas mix | none | 3$^{rd}$ stage |

Gas mix utilized was 80% N$_2$/10% CO$_2$/10% H$_2$

Results
1. The following table shows total cell growth (OD 600 nm) and the amount of Toxin A produced (ng/ml) and Toxin B produced (ng/ml) in the cultures subject to the indicated temperature and the indicated pH control (FIGS. 9A, 9B).

| Sample | OD@600 nm | Toxin A (ng/ml) | Toxin B (ng/ml) |
|---|---|---|---|
| 1$^{st}$ stage 18 h | 0.84 | N/A | N/A |
| 2$^{nd}$ stage 10 h | 1.92 | N/A | N/A |
| QA1 39° C. uncontrolled 18 h | 3.23 | 29892 | 18321 |
| QA2 39° C. pH 6.5 18 h | 3.24 | 32565 | 18445 |
| QA3 37° C. pH 6.35 18 h | 2.83 | 21827 | 9173 |
| QB1 37° C. pH 6.65 18 h | 3.32 | 33149 | 18508 |
| QB2 41° C. pH 6.35 18 h | 2.43 | 21537 | 13522 |
| QB3 41° C. pH 6.65 18 h | 3.14 | 25924 | 16784 |
| QA1 39° C. uncontrolled 21 h | 3.26 | 27314 | 13886 |
| QA2 39° C. pH 6.5 21 h | 3.20 | 30509 | 13658 |
| QA3 37° C. pH 6.35 21 h | 3.04 | 34317 | 16935 |
| QB1 37° C. pH 6.65 21 h | 3.41 | 24851 | 14450 |
| QB2 41° C. pH 6.35 21 h | 2.90 | 21176 | 16561 |
| QB3 41° C. pH 6.65 21 h | 2.95 | 28002 | 20790 |

2. Cell growth was higher in lower temperature and higher pH conditions. Toxin A production was higher in the low temperature (37° C.) and low pH (6.35) conditions. Toxin B production was higher in the high temperature (41° C.) and high pH (6.65) conditions. Lower toxin A yields were seen in high temperature and low pH conditions and lower toxin B yields were seen in low temperature and high pH conditions.

Conclusions

Optimal conditions for production of Toxin A and B are different. Since Toxin B availability is a limiting factor for the production of a vaccine product comprising Toxoids A and B (e.g., in a ratio of 3:2), conditions which favor Toxin B production may be preferred. Higher temperature (41° C.) and higher controlled pH (6.65) are the best conditions for Toxin B production. While these conditions are not the most optimal for Toxin A yields, Toxin A is produced and at a level above other conditions.

Example 11

This example includes data on the amount of toxin produced when *Clostridium difficile* is cultured in SYS basal media supplemented with D-Sorbitol (12 g/L) under a controlled a pH 6.5, and at various temperatures (33, 35, 37, 39, 41, 43° C.) and 2 g/L sodium bicarbonate.

The materials and methods utilized in this experiment were as set out in Example 6, except as noted below.

Materials

The composition of the SYS media for the first stage seed cultures was as described in Example 6. For the third stage cultures, an SYS media supplemented with Sorbitol was prepared having the following composition and using RODI-water:

SYS media + Sorbitol

| Component | Manufacturer/Part #/Lot # | Formulation (g/L) |
|---|---|---|
| $KH_2PO_4$ | J T Baker/3248-07/E29H22 | 0.9 |
| $Na_2PO_4$ | J T Baker/3827-01/B08143 | 5 |
| $NaHCO_3$ | J T Baker/3509-05/E05589 | 2 |
| Soy Peptone A3 SC | Organotechnie/130-127-00/102630 | 30 |
| Yeast Extract | BD Bacto/212720/8352570 | 20 |
| D-Sorbitol (70%) | Spectrum/S0220/WJ1030 | 17.1 ml |

Methods

III. Production Bioreactor 1. 6×1 L vessels (3rd stage vessels: QA1 to QA3, QB1 to QB3) were prepared in 2 sets (of 2 and 3). The desired temperature and pH control setpoints were implemented (see Table 9).
2. Prior to inoculation, bioreactors were sparged with an appropriate gas for 30 minutes at 300 mL/min (see Table 9).
3. 3rd stage cultures were incubated at the applicable temperature with no gassing for 21 hours.

TABLE 9

| Vessel No. | Volume (ml) | Ionc. (ml) | Temp (° C.) | pH Control | Sodium Bicarb (g/L) | Degas Gas | Sparge Gas | Culture Gas |
|---|---|---|---|---|---|---|---|---|
| B1 | 1600 | 4 | 37 | None | 5 | Gas mix | Gas mix | 1st stage |
| B2 | 1800 | 200 | 37 | None | 5 | Gas mix | Gas mix | 2nd stage |
| QA1 | 900 | 100 | 33 | 6.5 | 2 | 100% $CO_2$ | None | 3rd stage |
| QA2 | 900 | 100 | 35 | 6.5* | 2 | 100% $CO_2$ | None | 3rd stage |
| QA3 | 900 | 100 | 37 | 6.5 | 2 | 100% $CO_2$ | None | 3rd stage |
| QB1 | 900 | 100 | 39 | 6.5 | 2 | 100% $CO_2$ | None | 3rd stage |
| QB2 | 900 | 100 | 41 | 6.5 | 2 | 100% $CO_2$ | None | 3rd stage |
| QB3 | 900 | 100 | 43 | 6.5 | 2 | 100% $CO_2$ | None | 3rd stage |

*pH control for QA2 was not activated due to a problem with the base tubing. Gas mix utilized was 80% $N_2$/10% $CO_2$/10% $H_2$ Results 1. The following table shows total cell growth (OD 600 nm) and the amount of Toxin A produced (ng/ml) and Toxin B produced (ng/ml) in the cultures subject to the indicated temperature and the indicated pH control (FIGS. 10A, 10B, 10C, 10D).

| Sample | OD@600 nm | Toxin A (ng/ml) | Toxin B (ng/ml) |
|---|---|---|---|
| 1st stage 18 h | 1.31 | N/A | N/A |
| 2nd stage 10 h | 1.90 | N/A | N/A |
| QA1 19 h | 2.40 | 10956 | 5853 |
| QA2 19 h | 2.42 | 15409 | 9487 |
| QA3 19 h | 2.95 | 19723 | 13736 |
| QB1 19 h | 2.12 | 18425 | 16929 |
| QB2 19 h | 2.53 | 18465 | 18184 |
| QB3 19 h | 1.71 | 9981 | 9110 |
| QA1 22 h | 2.57 | 12200 | 8218 |
| QA2 22 h | 2.73 | 16895 | 10681 |
| QA3 22 h | 2.74 | 29124 | 22679 |
| QB1 22 h | 2.20 | 17686 | 16658 |
| QB2 22 h | 2.46 | 18730 | 22104 |
| QB3 22 h | 1.76 | 10160 | 9091 |

2. Cell growth decreases at temperatures higher than 37° C. Toxin A production is highest and similar within the range of 37-41° C. Toxin B yield increases almost linearly with increasing temperature from 37-41° C.

Conclusions

Culturing *C. difficile* at 37-41° C. is optimal for both Toxin A and B production. Culturing *C. difficile* at temperatures at the higher end of the 37-41° C. range favors increased Toxin B production.

Example 12

This example includes data on the amount of toxin produced when *Clostridium difficile* is cultured in SYS basal media supplemented with D-Sorbitol (12 g/L) using different inoculum concentrations (1%, 5%, and 10% of initial bioreactor volume) and under different pH conditions (controlled pH 6.5 and controlled at pH 6.5 with base-only).

The materials and methods utilized in this experiment were as set out in Example 6, except as noted below.

Materials

The composition of the SYS media for the first stage seed cultures was as described in Example 6. For the third stage cultures, an SYS media supplemented with Sorbitol was prepared having the following composition and using RODI-water:

| SYS media + Sorbitol | | |
|---|---|---|
| Component | Manufacturer/Part #/Lot # | Formulation (g/L) |
| $KH_2PO_4$ | J T Baker/3248-07/Y48478 | 0.9 |
| $Na_2PO_4$ | J T Baker/3827-01/B08143 | 5 |
| $NaHCO_3$ | J T Baker/3509-05/E05589 | 2 |
| Soy Peptone A3 SC | Organotechnie/130-127-00/18 | 30 |

| SYS media + Sorbitol | | |
|---|---|---|
| Component | Manufacturer/Part #/Lot # | Formulation (g/L) |
| Yeast Extract | BD Bacto/212720/8352570 | 20 |
| D-Sorbitol (70%) | Spectrum/S0220/WJ1030 | 17.1 ml (12 g/L) |

Methods

III. Production Bioreactor 1. 6×1 L vessels (3rd stage vessels: QA1 to QA3, QB1 to QB3) were prepared in 2 sets (of 2 and 3). The desired temperature and pH setpoints were implemented (see Table 11). For vessels QA1, QA2, and QA3, pH was set at 6.5 for control with base-only (5N NaOH). Base-only control involves the addition of base to the culture to adjust the culture pH to pH 6.5 in the event the culture pH becomes lower than 6.5. Under such control, the pH of the culture naturally decreases from the initial media pH (approximately pH 7.4) to pH 6.5.
2. Prior to inoculation, bioreactors were sparged with the applicable gas for 30 minutes at 300 mL/min (see Table 10) and then an overlay of nitrogen gas was added to the applicable vessels.
3. 3rd stage cultures were incubated at the applicable temperature for 24 hours.

TABLE 10

| Vessel No. | Volume (ml) | Inoc (ml) | Temp (° C.) | pH Control | Sodium Bicarb (g/L) | Degas Gas | Sparge Gas (overlay) | Culture Stage |
|---|---|---|---|---|---|---|---|---|
| B1 | 1600 | 4 | 37 | none | 5 | Gas mix | Gas mix | 1st stage |
| B2 | 1800 | 200 | 37 | none | 5 | Gas mix | Gas mix | 2nd stage |
| QA1 | 900 | 10 | 37 | Low end 6.5 | 2 | Nitrogen | (Nitrogen) | 3rd stage |
| QA2 | 900 | 50 | 37 | Low end 6.5 | 2 | Nitrogen | (Nitrogen) | 3rd stage |
| QA3 | 900 | 100 | 37 | Low end 6.5 | 2 | Nitrogen | (Nitrogen) | 3rd stage |
| QB1 | 900 | 10 | 37 | 6.5 | 2 | $CO_2$ | (Nitrogen) | 3rd stage |
| QB2 | 900 | 50 | 37 | 6.5 | 2 | $CO_2$ | (Nitrogen) | 3rd stage |
| QB3 | 900 | 100 | 37 | 6.5 | 2 | $CO_2$ | (Nitrogen) | 3rd stage |

Results

Figure 11:
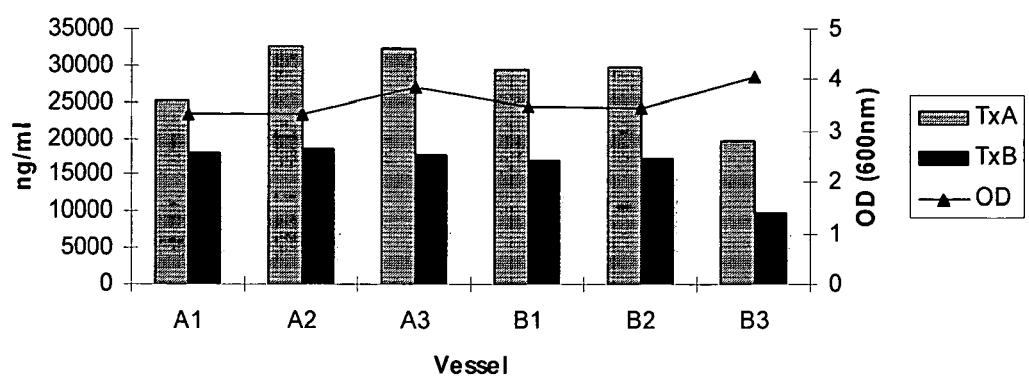
FIG. 11 is a graph showing the amount of Toxin A and Toxin B produced (ng/ml) in comparison to cell growth (OD600) in cultures subject to the indicated pH condition and inoculated with the indicated % of inoculum.

The following table shows total cell growth (OD 600 nm) and the amount of Toxin A produced (ng/ml) and Toxin B produced (ng/ml) in the cultures subject to the indicated temperature and the indicated pH control (FIG. 11).

| Sample | Cell Growth by OD600 Measurement | | | | Toxin A Concentration By ELISA | | | Toxin B Concentration by ELISA | | |
|---|---|---|---|---|---|---|---|---|---|---|
| | 0 h | 16 h | 20 h | 24 h | 16 h | 20 h | 24 h | 16 h | 20 h | 24 h |
| QA1 low end pH 6.5, 1% inoc | 0.013 | 4.24 | 4.75 | 4.46 | 12840 | 23135 | 24056 | 7006.1 | 15679.21 | 16010.07 |
| QA2 low end pH 6.5, 5% inoc | 0.089 | 4.71 | 4.64 | 4.62 | 17831 | 24387 | 26873 | 9599.37 | 13386.5 | 17642.25 |

-continued

| | Cell Growth by OD600 Measurement | | | | Toxin A Concentration By ELISA | | | Toxin B Concentration by ELISA | | |
|---|---|---|---|---|---|---|---|---|---|---|
| Sample | 0 h | 16 h | 20 h | 24 h | 16 h | 20 h | 24 h | 16 h | 20 h | 24 h |
| QA3 low end pH 6.5, 10% inoc | 0.182 | 4.49 | 4.76 | 4.39 | 19978 | 34845 | 29240 | 12300.11 | 18254.64 | 16550.53 |
| QB1 pH 6.5, 1% inoc | −0.016 | 3.11 | 4.08 | 4.25 | 13757 | 28501 | 34720 | 9002.91 | 16828.93 | 25691.37 |
| QB2 pH 6.5, 5% inoc | 0.062 | 3.22 | 4.29 | 4.59 | 19815 | 33186 | 34216 | 11500.96 | 21603.89 | 21967.57 |
| QB3 pH 6.5, 10% inoc | 0.153 | 3.56 | 4.5 | 4.46 | 26469 | 35068 | 44541 | 16546.46 | 21293.34 | 34246.13 |

In this experiment, a 10 L vessel (Sartorius) was also utilized. The vessel was autoclaved and connected to the Biostat system and the following conditions were set: 37° C. and agitation (stirring) at 100 rpm. Culture pH was not controlled. The vessel was filled with 9 L of the SYS media also utilized in filling the 1 L fermenters (i.e., SYS media with 12 g/L sorbitol and 2 g/L $Na_2HCO_3$). The vessel was then de-gassed using Nitrogen gas and inoculated with 1 L of the Seed Bioreactor 2 culture. Toxin production and cell growth (OD) was measured following an 18 hour incubation: Toxin A (24533 ng/ml); Toxin B (14837 ng/ml); 2.94 OD(600 nm).

A 10 L vessel was also included in two of the experiments set out above (i.e., Examples 10 and 11) and was prepared, inoculated, and cultured similarly (except de-gassing was done with gas mix 80% $N_2$/10% $CO_2$/10% $H_2$ and agitation was set at 75 rpm). The measured toxin production and cell growth following an 18 hour incubation was as follows: in Example 10, Toxin A (29605 ng/ml); Toxin B (10732 ng/ml); 2.95 OD(600 nm); in Example 11, Toxin A (25681 ng/ml); Toxin B (24898 ng/ml); 3.17 OD (600 nm). In a separate experiment, toxin production and cell growth in a 10 L culture with SYS media (with 12 g/L sorbitol and 2 g/L $Na_2HCO_3$) under similar conditions (i.e., a 10% inoculum concentration, culture temperature of 37° C. and 50 rpm agitation) was similar: Toxin A (21090 ng/ml); Toxin B (12228 ng/ml) and 3.02 OD (600 nm).

Conclusions

Similar toxin yields may be achieved by using inoculum rates lower than 10% although the culture duration may need to be increased. Inoculations of 1% and 5% achieved toxin yields >30 μg/ml for toxin A and >15 μg/ml of toxin B after 20 hours.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

All publications and patent applications mentioned in this specification are herein incorporated by reference to the same extent as if each independent publication or patent application was specifically and individually indicated to be incorporated by reference in their entirety.

What is claimed is:

1. A method for obtaining one or more *Clostridium difficile* (*C. difficilel*) toxins comprising the steps of:
   (a) preparing an aqueous growth medium comprising soy peptone and D-sorbitol;
   (b) inoculating the medium with a *C. difficile* bacterium;
   (c) culturing the inoculated medium under conditions which facilitate growth of bacterium and toxin production; and
   (d) isolating the one or more *C. difficile* toxins from the growth medium.

2. The method of claim 1, wherein:
   (a) in step (a) the growth medium comprises: (i) between 10 and 20 g/L soy peptone; (ii) between 10 and 30 g/I yeast extract; between 2 and 5 g/L $NaHCO_3$; between 1 and 10 g/L sodium phosphate, dibasic; between 1 and 10 g/L potassium phosphate, monobasic; and between 6 and 20 g/L D-sorbitol;
   (b) in step (c) the inoculated medium is at pH of between 6.35 and 6.65 during culturing;
   (c) in step (c) the culturing of the inoculated medium takes place at 37° C. to 41° C.;
   (d) the culturing of the inoculated media is carried out under anaerobic conditions; or
   (e) in step (b) the medium is inoculated with an aqueous *C. difficile* culture.

3. The method of claim 1, further comprising the step of detoxifying the isolated one or more *C. difficile* toxins to prepare one or more toxoids.

4. The method of claim 3, wherein:
   (a) steps (b) and (c) are repeated more than once, with inoculation into fresh growth medium in each repeat;
   (b) wherein step (c) takes place at 37° C. to 41° C.;
   (c) step (d) comprises: removing from the growth medium viable *C. difficile* organisms and spores, separating the one or more toxins from the growth media, and purifying the one or more toxins; or
   (d) step (e) comprises reacting the one or more toxins with the addition of formaldehyde.

5. The method of claim 1, wherein:
   (a) the growth medium further comprises:
   at least one additive selected from the group consisting of chromium trioxide, clindamycin, ascorbic acid, butyric acid, D(+)xylose, sucrose, and a combination of azaserine, adenosine, and biotin.

6. The method of claim 5, wherein the growth medium comprises:
   (a) at least two of said additives;
   (b) D-sorbitol at a concentration between 6 g/L and 20 g/L;
   (c) D-sorbitol at a concentration of 12 g/L;
   (d) chromium trioxide at a concentration between 40 and 60 mg/L;

(e) chromium trioxide at a concentration of 50 mg/L;
(f) clindamycin at a concentration between 0.4 and 0.6 mg/L;
(g) clindamycin at a concentration of 0.5 mg/L;
(h) ascorbic acid at a concentration between 2.5 g/L and 10 g/L;
(i) ascorbic acid at a concentration selected from 2.5 g/L and 10 g/L;
(j) butyric acid at a concentration between 30 mM and 60 mM;
(k) butyric acid at a concentration selected from 30 mM and 60 mM;
(l) D(+)xylose at a concentration between 6 and 10 g/L;
(m) D(+)xylose at a concentration of 6 g/L;
(n) adenosine at a concentration of between 0.8 and 1.2 mM, biotin at a concentration of between 40 and 60 nM, and azaserine at a concentration between 15 and 50 μM; or
(o) adenosine at a concentration of 1 mM, biotin at a concentration of 50 nM, and
azaserine at a concentration of 50 μM.

7. The method of claim 6, wherein the growth medium comprises soy peptone, yeast extract, $KH_2PO_4$, $Na_2HPO_4$, and $NaHCO_3$, and wherein the culture is at a pH of between 6.35 and 7.45.

8. A method of enhancing the production from a *C. difficile* culture of Toxin B relative to the production of Toxin A comprising the steps of:
(a) preparing an aqueous growth medium comprising soy peptone and D-sorbitol;
(b) inoculating the medium with a *C. difficile* bacterium; and
(c) culturing the inoculated medium at 37° C. to 41° C.

9. The method of claim 8, wherein:
(a) step (c) takes place at 37° C. and at a pH of pH 6.5;
(b) the pH of step (c) is controlled at a pH between pH 6.35 to pH 6.65; or
(c) the aqueous growth medium of step (a) further comprises between 10 and 20 g/L soy peptone; and between 6 and 20 g/L D-sorbitol.

10. The method of claim 8, wherein:
(a) the production of Toxin A relative to Toxin B is less than 3:1;
(b) the production of Toxin A relative to Toxin B is less than 2:1; or
(c) the production of Toxin A relative to Toxin B is equal to or less than 1.5:1.

\* \* \* \* \*